United States Patent
Gross et al.

(10) Patent No.: US 10,383,685 B2
(45) Date of Patent: Aug. 20, 2019

(54) TECHNIQUES FOR USE WITH NERVE TISSUE

(71) Applicant: RAINBOW MEDICAL LTD., Herzliya (IL)

(72) Inventors: Yossi Gross, Moshav Mazor (IL); Yehuda Zadok, Holon (IL)

(73) Assignee: PYTHAGORAS MEDICAL LTD., Herzliya (IL)

( * ) Notice: Subject to any disclaimer, the term of this patent is extended or adjusted under 35 U.S.C. 154(b) by 416 days.

(21) Appl. No.: 15/147,081

(22) Filed: May 5, 2016

(65) Prior Publication Data

US 2016/0324572 A1    Nov. 10, 2016

Related U.S. Application Data

(60) Provisional application No. 62/158,139, filed on May 7, 2015.

(51) Int. Cl.
*A61B 18/12*    (2006.01)
*A61B 18/14*    (2006.01)
(Continued)

(52) U.S. Cl.
CPC ........ *A61B 18/1492* (2013.01); *A61B 5/0215* (2013.01); *A61B 18/1206* (2013.01); *A61B 5/024* (2013.01); *A61B 5/02007* (2013.01); *A61B 5/4848* (2013.01); *A61B 5/6852* (2013.01); *A61B 2018/00214* (2013.01); *A61B 2018/00404* (2013.01);
(Continued)

(58) Field of Classification Search
CPC ................ A61B 5/4848; A61B 5/0538; A61B 2018/00511
See application file for complete search history.

(56) References Cited

U.S. PATENT DOCUMENTS 4,106,488 A    8/1978    Gordon
4,569,836 A    2/1986    Gordon
(Continued)

FOREIGN PATENT DOCUMENTS

CA    2900160    8/2014
CA    2956945    2/2016
(Continued)

OTHER PUBLICATIONS

Buch E et al., "Intra-pericardial balloon retraction of the left atrium: A novel method to prevent esophageal injury during catheter ablation," Heart Rhythm 2008;5:1473-1475.
(Continued)

*Primary Examiner* — Jaymi E Della
*Assistant Examiner* — Sean W Collins
(74) *Attorney, Agent, or Firm* — Sughrue Mion, PLLC

(57) ABSTRACT

A method is provided, comprising: (1) applying an excitatory current to renal nerve fibers of a subject; (2) determining a change in a parameter of the subject in response to the excitatory current, the parameter being a fastest rate of increase in arterial pressure during a systolic upstroke of an arterial pressure wave of the subject; (3) in response to the change, deciding whether to ablate the renal nerve fibers; and (4) in response to the deciding, applying ablation energy to the renal nerve fibers. Other embodiments are also described.

7 Claims, 10 Drawing Sheets

(51) Int. Cl.

| | | |
|---|---|---|
| *A61B 5/0215* | (2006.01) | |
| *A61B 18/00* | (2006.01) | |
| *A61B 5/00* | (2006.01) | |
| *A61B 5/02* | (2006.01) | |
| *A61B 5/024* | (2006.01) | |
| *A61B 90/00* | (2016.01) | |

(52) U.S. Cl.
CPC .............. *A61B 2018/00434* (2013.01); *A61B 2018/00511* (2013.01); *A61B 2018/00577* (2013.01); *A61B 2018/00642* (2013.01); *A61B 2018/00702* (2013.01); *A61B 2018/00773* (2013.01); *A61B 2090/064* (2016.02); *A61B 2505/05* (2013.01); *A61B 2562/0247* (2013.01)

(56) References Cited

U.S. PATENT DOCUMENTS

| | | | |
|---|---|---|---|
| 4,619,247 | A | 10/1986 | Inoue |
| 5,215,086 | A | 6/1993 | Terry, Jr. et al. |
| 5,251,634 | A | 10/1993 | Weinberg |
| 5,697,377 | A | 12/1997 | Wittkampf |
| 5,735,280 | A | 4/1998 | Sherman et al. |
| 5,776,063 | A | 7/1998 | Dittrich et al. |
| 5,807,285 | A | 9/1998 | Vaitekunas |
| 5,817,022 | A | 10/1998 | Vesely |
| 5,827,216 | A | 10/1998 | Igo et al. |
| 6,050,943 | A | 4/2000 | Slayton |
| 6,064,902 | A | 5/2000 | Haissaguerre et al. |
| 6,117,101 | A | 9/2000 | Diederich |
| 6,128,523 | A | 10/2000 | Bechtold |
| 6,161,048 | A | 12/2000 | Sluijter |
| 6,219,577 | B1 | 4/2001 | Brown |
| 6,233,477 | B1 | 5/2001 | Chia |
| 6,241,727 | B1 | 6/2001 | Tu |
| 6,246,899 | B1 | 6/2001 | Chia |
| 6,361,500 | B1 | 3/2002 | Masters |
| 6,405,732 | B1 | 6/2002 | Edwards |
| 6,425,877 | B1 | 7/2002 | Edwards |
| 6,440,077 | B1 | 8/2002 | Jung |
| 6,485,431 | B1 * | 11/2002 | Campbell .............. A61B 5/02 600/500 |
| 6,522,926 | B1 | 2/2003 | Kieval |
| 6,526,318 | B1 | 2/2003 | Ansarinia |
| 6,605,084 | B2 | 8/2003 | Acker et al. |
| 6,635,054 | B2 | 10/2003 | Fjield et al. |
| 6,641,579 | B1 | 11/2003 | Bernardi |
| 6,659,950 | B2 | 12/2003 | Taheri |
| 6,671,556 | B2 | 12/2003 | Osorio et al. |
| 6,684,105 | B2 | 1/2004 | Cohen et al. |
| 6,685,639 | B1 | 2/2004 | Wang |
| 6,692,490 | B1 | 2/2004 | Edwards |
| 6,701,931 | B2 | 3/2004 | Sliwa et al. |
| 6,736,835 | B2 | 5/2004 | Pellegrino |
| 6,740,040 | B1 | 5/2004 | Mandrusov |
| 6,805,129 | B1 | 10/2004 | Pless et al. |
| 6,845,267 | B2 | 1/2005 | Harrison |
| 7,001,336 | B2 | 2/2006 | Mandrusov |
| 7,022,105 | B1 | 4/2006 | Edwards |
| 7,037,306 | B2 | 5/2006 | Podany et al. |
| 7,149,574 | B2 | 12/2006 | Yun |
| 7,162,303 | B2 | 1/2007 | Levin |
| 7,226,440 | B2 | 6/2007 | Gelfand et al. |
| 7,311,701 | B2 | 12/2007 | Gifford et al. |
| 7,326,201 | B2 | 2/2008 | Fjield et al. |
| 7,430,449 | B2 | 9/2008 | Aldrich |
| 7,499,747 | B2 | 3/2009 | Kieval |
| 7,510,536 | B2 | 3/2009 | Foley |
| 7,553,284 | B2 | 6/2009 | Vaitekunas |
| 7,565,191 | B2 | 7/2009 | Burbank et al. |
| 7,617,005 | B2 | 11/2009 | Demarais |
| 7,647,115 | B2 | 1/2010 | Levin et al. |
| 7,653,438 | B2 | 1/2010 | Deem |
| 7,662,099 | B2 | 2/2010 | Podany et al. |
| 7,684,865 | B2 | 3/2010 | Aldrich |
| 7,706,882 | B2 | 4/2010 | Francischelli |
| 7,717,948 | B2 | 5/2010 | Demarais |
| 7,787,946 | B2 | 8/2010 | Stahmann et al. |
| 7,840,271 | B2 | 11/2010 | Kieval |
| 7,853,333 | B2 | 12/2010 | Demarais |
| 7,854,733 | B2 | 12/2010 | Govari |
| 7,901,359 | B2 | 3/2011 | Mandrusov |
| 7,974,696 | B1 | 7/2011 | DiLorenzo |
| 8,197,409 | B2 | 6/2012 | Foley |
| 8,391,970 | B2 | 3/2013 | Tracey et al. |
| 8,585,601 | B2 | 11/2013 | Sverdlik et al. |
| 8,696,581 | B2 | 4/2014 | Sverdlik et al. |
| 8,702,619 | B2 | 4/2014 | Wang |
| 9,014,821 | B2 | 4/2015 | Wang |
| 9,028,417 | B2 | 5/2015 | Sverdlik et al. |
| 9,381,063 | B2 | 7/2016 | Gang et al. |
| 9,408,549 | B2 | 8/2016 | Brockway et al. |
| 9,439,598 | B2 | 9/2016 | Shimada et al. |
| 9,566,456 | B2 | 2/2017 | Sverdlik et al. |
| 9,999,463 | B2 | 6/2018 | Puryear et al. |
| 2001/0003798 | A1 | 6/2001 | McGovern |
| 2001/0007940 | A1 | 7/2001 | Tu |
| 2002/0091427 | A1 | 7/2002 | Rappaport |
| 2002/0147446 | A1 | 10/2002 | Ein-Gal |
| 2002/0173688 | A1 | 11/2002 | Chen |
| 2002/0193787 | A1 | 12/2002 | Qin et al. |
| 2003/0018256 | A1 | 1/2003 | Sasaki |
| 2003/0045909 | A1 | 3/2003 | Gross et al. |
| 2003/0055421 | A1 | 3/2003 | West |
| 2003/0069590 | A1 | 4/2003 | Rabiner |
| 2003/0013968 | A1 | 6/2003 | Fjield |
| 2004/0034339 | A1 | 2/2004 | Stoller |
| 2004/0038857 | A1 | 2/2004 | Tracey |
| 2004/0097788 | A1 | 5/2004 | Mourlas |
| 2004/0122494 | A1 | 6/2004 | Eggers et al. |
| 2004/0162507 | A1 | 8/2004 | Govari et al. |
| 2004/0162550 | A1 | 8/2004 | Govari et al. |
| 2004/0193021 | A1 | 9/2004 | Savage |
| 2005/0020921 | A1 | 1/2005 | Glassell |
| 2005/0080469 | A1 | 4/2005 | Larson et al. |
| 2005/0165298 | A1 | 7/2005 | Larson |
| 2005/0192638 | A1 | 9/2005 | Gelfand |
| 2005/0203410 | A1 | 9/2005 | Jenkins |
| 2005/0222554 | A1 | 10/2005 | Wallace et al. |
| 2005/0251125 | A1 | 11/2005 | Pless |
| 2005/0288651 | A1 | 12/2005 | Van Tassel et al. |
| 2005/0288730 | A1 | 12/2005 | Deem et al. |
| 2006/0009753 | A1 | 1/2006 | Fjield et al. |
| 2006/0041277 | A1 | 2/2006 | Deem |
| 2006/0058711 | A1 | 3/2006 | Harhen et al. |
| 2006/0100514 | A1 | 5/2006 | Lopath |
| 2006/0184048 | A1 | 8/2006 | Saadat |
| 2006/0206150 | A1 | 9/2006 | Demarais |
| 2006/0212076 | A1 | 9/2006 | Demarais |
| 2006/0212078 | A1 | 9/2006 | Demarais |
| 2006/0241523 | A1 | 10/2006 | Sinelnikov et al. |
| 2006/0265014 | A1 | 11/2006 | Demarais |
| 2006/0265015 | A1 | 11/2006 | Demarais |
| 2006/0271111 | A1 | 11/2006 | Demarais |
| 2006/0276852 | A1 | 12/2006 | Demarais |
| 2006/0287648 | A1 | 12/2006 | Schwartz |
| 2007/0004984 | A1 | 1/2007 | Crum et al. |
| 2007/0021803 | A1 | 1/2007 | Deem |
| 2007/0038259 | A1 | 2/2007 | Kieval |
| 2007/0060972 | A1 | 3/2007 | Kieval |
| 2007/0093420 | A1 | 4/2007 | Yeomans |
| 2007/0112327 | A1 | 5/2007 | Lee |
| 2007/0129760 | A1 | 6/2007 | Demarais |
| 2007/0129761 | A1 | 6/2007 | Demarais |
| 2007/0133849 | A1 | 6/2007 | Young et al. |
| 2007/0135875 | A1 | 6/2007 | Demarais |
| 2007/0142879 | A1 | 6/2007 | Greenberg |
| 2007/0162085 | A1 | 6/2007 | DiLorenzo |
| 2007/0167984 | A1 | 6/2007 | Kieval |
| 2007/0167913 | A1 | 7/2007 | Elkins et al. |
| 2007/0173899 | A1 | 7/2007 | Levin et al. |
| 2007/0191906 | A1 | 8/2007 | Caparso |
| 2007/0203549 | A1 | 8/2007 | Demarais |
| 2007/0239077 | A1 | 10/2007 | Azhari et al. |

(56) References Cited

U.S. PATENT DOCUMENTS

| | | |
|---|---|---|
| 2007/0265610 A1 | 11/2007 | Thapliyal et al. |
| 2007/0265687 A1 | 11/2007 | Deem |
| 2007/0282407 A1 | 12/2007 | Demarais |
| 2008/0004614 A1 | 1/2008 | Burdette |
| 2008/0015445 A1 | 1/2008 | Saadat |
| 2008/0033415 A1 | 2/2008 | Rieker et al. |
| 2008/0039746 A1 | 2/2008 | Francischelli |
| 2008/0058682 A1 | 3/2008 | Azhari et al. |
| 2008/0058702 A1 | 3/2008 | Arndt |
| 2008/0071173 A1 | 3/2008 | Aldrich |
| 2008/0091109 A1 | 4/2008 | Abraham |
| 2008/0108984 A1 | 5/2008 | Burdette |
| 2008/0125819 A1 | 5/2008 | Ben-David et al. |
| 2008/0140180 A1 | 6/2008 | Dolan et al. |
| 2008/0172104 A1 | 7/2008 | Kieval |
| 2008/0183248 A1 | 7/2008 | Rezai |
| 2008/0215111 A1 | 9/2008 | Kieval |
| 2008/0255449 A1 | 10/2008 | Sinelnikov |
| 2008/0255642 A1 | 10/2008 | Zarins |
| 2008/0281379 A1 | 11/2008 | Wesselink |
| 2008/0288017 A1 | 11/2008 | Kieval |
| 2008/0288031 A1 | 11/2008 | Kieval |
| 2008/0306570 A1 | 12/2008 | Rezai |
| 2008/0312521 A1 | 12/2008 | Solomon |
| 2008/0319513 A1 | 12/2008 | Pu |
| 2009/0024195 A1 | 1/2009 | Rezai et al. |
| 2009/0048514 A1 | 2/2009 | Azhari |
| 2009/0062790 A1 | 3/2009 | Malchano |
| 2009/0062873 A1 | 3/2009 | Wu et al. |
| 2009/0076409 A1 | 3/2009 | Wu |
| 2009/0112133 A1 | 4/2009 | Deisseroth |
| 2009/0118780 A1 | 5/2009 | DiLorenzo |
| 2009/0137900 A1 | 5/2009 | Bonner et al. |
| 2009/0155336 A1 | 6/2009 | Rezai |
| 2009/0187230 A1 | 6/2009 | DiLorenzo |
| 2009/0192506 A9 | 7/2009 | Vaska et al. |
| 2009/0234407 A1 | 9/2009 | Hastings et al. |
| 2009/0247912 A1 | 10/2009 | Warnking |
| 2009/0270741 A1 | 10/2009 | Vanney et al. |
| 2009/0275827 A1 | 11/2009 | Aiken et al. |
| 2009/0287274 A1 | 11/2009 | Ridder |
| 2009/0326511 A1 | 12/2009 | Shivkumar |
| 2010/0004704 A1 | 1/2010 | Mazgalev |
| 2010/0010567 A1 | 1/2010 | Deem |
| 2010/0036292 A1 | 2/2010 | Darlington et al. |
| 2010/0042170 A1 | 2/2010 | Caparso |
| 2010/0105993 A1 | 4/2010 | Hassan |
| 2010/0113928 A1 | 5/2010 | Thapliyal |
| 2010/0130836 A1 | 5/2010 | Malchano |
| 2010/0137860 A1 | 6/2010 | Demarais |
| 2010/0137949 A1 | 6/2010 | Mazgalev |
| 2010/0137952 A1 | 6/2010 | Demarais et al. |
| 2010/0145428 A1 | 6/2010 | Cameron |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais |
| 2010/0191112 A1 | 7/2010 | Demarais |
| 2010/0204741 A1 | 8/2010 | Tweden |
| 2010/0217162 A1 | 8/2010 | Francischelli |
| 2010/0217369 A1 | 8/2010 | Gross |
| 2010/0222851 A1 | 9/2010 | Deem |
| 2010/0222854 A1 | 9/2010 | Demarais |
| 2010/0234728 A1 | 9/2010 | Foley |
| 2010/0256436 A1 | 10/2010 | Partsch |
| 2010/0268297 A1 | 10/2010 | Neisz |
| 2010/0305392 A1 | 12/2010 | Gross et al. |
| 2010/0312094 A1 | 12/2010 | Guttman et al. |
| 2011/0009734 A1 | 1/2011 | Foley |
| 2011/0015548 A1 | 1/2011 | Aldrich |
| 2011/0022133 A1 | 1/2011 | Bradford |
| 2011/0040171 A1 | 2/2011 | Foley |
| 2011/0040214 A1 | 2/2011 | Foley |
| 2011/0060324 A1 | 3/2011 | Wu |
| 2011/0092781 A1 | 4/2011 | Gertner |
| 2011/0092880 A1 | 4/2011 | Gertner |
| 2011/0112394 A1 | 5/2011 | Mishelevich |
| 2011/0112400 A1 | 5/2011 | Emery |
| 2011/0118598 A1 | 5/2011 | Gertner |
| 2011/0118600 A1 | 5/2011 | Gertner |
| 2011/0118725 A1 | 5/2011 | Mayse |
| 2011/0137149 A1 | 6/2011 | Gertner |
| 2011/0137298 A1 | 6/2011 | Chen |
| 2011/0172527 A1 | 6/2011 | Gertner |
| 2011/0172528 A1 | 6/2011 | Gertner |
| 2011/0172529 A1 | 6/2011 | Gertner |
| 2011/0178570 A1 | 6/2011 | Demarais |
| 2011/0184337 A1 | 6/2011 | Evans |
| 2011/0178541 A1 | 7/2011 | Azhari |
| 2011/0184322 A1 | 7/2011 | Brawer |
| 2011/0196248 A1 | 8/2011 | Grunwald |
| 2011/0207758 A1 | 8/2011 | Sobotka et al. |
| 2011/0208173 A1 | 8/2011 | Sobotka et al. |
| 2011/0208175 A1 | 8/2011 | Sobotka et al. |
| 2011/0251524 A1 | 10/2011 | Azhari |
| 2011/0257523 A1 | 10/2011 | Hastings et al. |
| 2011/0257564 A1 | 10/2011 | Demarais et al. |
| 2011/0257641 A1 | 10/2011 | Hastings et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0282203 A1 | 11/2011 | Tsoref |
| 2011/0282249 A1 | 11/2011 | Tsoref |
| 2011/0306851 A1 | 12/2011 | Wang |
| 2012/0029500 A1 | 2/2012 | Jenson |
| 2012/0029505 A1 | 2/2012 | Jenson |
| 2012/0029509 A1 | 2/2012 | Smith et al. |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0089047 A1 | 4/2012 | Ryba et al. |
| 2012/0095371 A1 | 4/2012 | Sverdlik et al. |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0130363 A1 | 5/2012 | Kim |
| 2012/0150049 A1 | 6/2012 | Zielinski et al. |
| 2012/0157992 A1 | 6/2012 | Smith et al. |
| 2012/0172680 A1 | 7/2012 | Gelfand et al. |
| 2012/0191079 A1 | 7/2012 | Moll et al. |
| 2012/0197198 A1 | 8/2012 | Demarais |
| 2012/0197243 A1 | 8/2012 | Sherman et al. |
| 2012/0265198 A1 | 10/2012 | Crow et al. |
| 2012/0265227 A1 | 10/2012 | Sverdlik et al. |
| 2012/0290024 A1 | 11/2012 | Zhang et al. |
| 2012/0296240 A1 | 11/2012 | Azhari |
| 2012/0296329 A1 | 11/2012 | Ng |
| 2013/0012866 A1 | 1/2013 | Deem |
| 2013/0013024 A1 | 1/2013 | Levin |
| 2013/0085489 A1 | 4/2013 | Fain et al. |
| 2013/0103028 A1 | 4/2013 | Tsoref |
| 2013/0131743 A1 | 5/2013 | Yamasaki et al. |
| 2013/0165926 A1 | 6/2013 | Mathur |
| 2013/0204242 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218029 A1 | 8/2013 | Cholette et al. |
| 2013/0218054 A1 | 8/2013 | Sverdlik et al. |
| 2013/0218068 A1 | 8/2013 | Sverdlik et al. |
| 2013/0231655 A1 | 9/2013 | Budzelaar et al. |
| 2013/0274614 A1* | 10/2013 | Shimada .......... A61B 5/4836 600/483 |
| 2013/0274735 A1 | 10/2013 | Hastings et al. |
| 2013/0289369 A1 | 10/2013 | Margolis |
| 2013/0303876 A1 | 11/2013 | Gelfand et al. |
| 2013/0310674 A1 | 11/2013 | Deno et al. |
| 2013/0310823 A1 | 11/2013 | Gelfand et al. |
| 2013/0322724 A1 | 12/2013 | Florent et al. |
| 2013/0324987 A1 | 12/2013 | Leung et al. |
| 2013/0324989 A1 | 12/2013 | Leung et al. |
| 2013/0331813 A1 | 12/2013 | Barbut et al. |
| 2014/0005706 A1 | 1/2014 | Gelfand et al. |
| 2014/0012133 A1 | 1/2014 | Sverdlik et al. |

(56) References Cited

U.S. PATENT DOCUMENTS

| | | |
|---|---|---|
| 2014/0018788 A1 | 1/2014 | Engelman et al. |
| 2014/0088561 A1 | 3/2014 | Levin et al. |
| 2014/0128865 A1 | 5/2014 | Gross |
| 2014/0194866 A1 | 7/2014 | Wang |
| 2014/0213873 A1 | 7/2014 | Wang |
| 2014/0221805 A1 | 8/2014 | Wang |
| 2014/0243809 A1 | 8/2014 | Gelfand et al. |
| 2014/0257263 A1 | 9/2014 | Azamian et al. |
| 2014/0276036 A1 | 9/2014 | Collins et al. |
| 2014/0276063 A1 | 9/2014 | Park et al. |
| 2014/0276742 A1 | 9/2014 | Nabutovsky et al. |
| 2014/0288551 A1 | 9/2014 | Bharmi et al. |
| 2015/0011843 A1 | 1/2015 | Toth et al. |
| 2015/0045649 A1 | 2/2015 | O'Dea et al. |
| 2015/0073400 A1 | 3/2015 | Sverdlik et al. |
| 2015/0148601 A1 | 5/2015 | Weiner et al. |
| 2015/0164401 A1 | 6/2015 | Toth et al. |
| 2015/0173673 A1 | 6/2015 | Toth et al. |
| 2015/0216590 A1 | 8/2015 | Wang et al. |
| 2015/0224326 A1 | 8/2015 | Toth et al. |
| 2015/0245867 A1 | 9/2015 | Gross |
| 2015/0257779 A1 | 9/2015 | Sinelnikov et al. |
| 2015/0289929 A1 | 10/2015 | Toth et al. |
| 2015/0297113 A1 | 10/2015 | Kassab et al. |
| 2015/0297139 A1 | 10/2015 | Toth |
| 2016/0000499 A1 | 1/2016 | Lennox et al. |
| 2016/0106498 A1 | 4/2016 | Highsmith et al. |
| 2016/0113699 A1 | 4/2016 | Sverdlik et al. |
| 2016/0128767 A1 | 5/2016 | Azamian et al. |
| 2016/0324572 A1 | 11/2016 | Gross et al. |
| 2016/0338773 A1 | 11/2016 | Shimada et al. |
| 2017/0007157 A1 | 1/2017 | Gross et al. |
| 2017/0007158 A1 | 1/2017 | Gross et al. |
| 2017/0027460 A1 | 2/2017 | Shimada et al. |
| 2017/0035310 A1 | 2/2017 | Shimada et al. |
| 2017/0056104 A1* | 3/2017 | Asirvatham ....... A61B 18/1492 |
| 2017/0172651 A1 | 6/2017 | Gross et al. |
| 2018/0221087 A1 | 8/2018 | Puryear et al. |
| 2018/0280082 A1 | 10/2018 | Puryear et al. |

FOREIGN PATENT DOCUMENTS

| | | |
|---|---|---|
| CN | 102551878 A | 7/2012 |
| CN | 203089369 U | 7/2013 |
| EP | 2460486 | 6/2012 |
| WO | 1999/40957 | 8/1999 |
| WO | 03/097162 | 11/2003 |
| WO | 2006/072928 | 7/2006 |
| WO | 07/134258 | 11/2007 |
| WO | 2008/003058 | 1/2008 |
| WO | 2009/073208 | 6/2009 |
| WO | 2010/067360 | 6/2010 |
| WO | 2011/024159 | 3/2011 |
| WO | 2011/141918 | 11/2011 |
| WO | 2012/100211 | 7/2012 |
| WO | 2012/120495 | 9/2012 |
| WO | 2012/122157 | 9/2012 |
| WO | 2013/030738 | 3/2013 |
| WO | 2013/030743 | 3/2013 |
| WO | 2013/049601 | 4/2013 |
| WO | 2013/111136 | 8/2013 |
| WO | 2013/121424 | 8/2013 |
| WO | 2013/157009 | 10/2013 |
| WO | 2014/029355 | 2/2014 |
| WO | 2014/068577 | 5/2014 |
| WO | 2014/071223 | 5/2014 |
| WO | 2014/123512 | 8/2014 |
| WO | 2014/160832 | 10/2014 |
| WO | 2014/175853 | 10/2014 |
| WO | 2015/057696 | 4/2015 |
| WO | 2015/138225 | 9/2015 |
| WO | 2015/170281 | 11/2015 |
| WO | 2015/175948 | 11/2015 |

OTHER PUBLICATIONS

Cassak D, "Endosense: Facing technology and financing challenges in AF," In-Vivo: The Business & Medicine Report, 36-44, Mar. 2010.

Di Biase L et al., "Prevention of phrenic nerve injury during epicardial ablation: Comparison of methods for separating the phrenic nerve from the epicardial surface," Heart Rhythm 2009;6:957-961.

Matsuo S et al., "Novel technique to prevent left phrenic nerve injury during epicardial catheter ablation," Circulation 2008;117;e471.

Nakahara S et al., "Intrapericardial balloon placement for prevention of collateral injury during catheter ablation of the left atrium in a porcine model," Heart Rhythm 2010;7:81-87.

Shen J et al., "The surgical treatment of atrial fibrillation Heart Rhythm," vol. 6, No. 8S, August Supplement 2009.

Sacher F et al., "Phrenic Nerve Injury After Catheter Ablation of Atrial Fibrillation," Indian Pacing Electrophysiol J. Jan.- Mar. 2007; 7(1): 1-6.

A Restriction Requirement dated Feb. 25, 2013, which issued during the prosecution of U.S. Appl. No. 12/780,240.

Tanaka S et al., "Development of a new vascular endoscopic system for observing inner wall of aorta using intermittent saline jet" World Congress on Medical Physics and Biomedical Engineering, Sep. 7-12, 2009, Munich, Germany.

Tearney GJ et al., "Three-Dimensional coronary artery microscopy by intracoronary optical frequency domain imaging" JACC Cardiovasc Imaging. Nov. 2008; 1(6): 752-761.

An Office Action dated Aug. 21, 2015, which issued during the prosecution of U.S. Appl. No. 13/771,853.

William E. Cohn, et al., "Contrast pericardiography facilitates intrapericardial navigation under fluoroscopy", Ann Thorac Surg 2010; 90: 1537-40. Accepted for publication Jun. 7, 2010.

Srijoy Mahapatra, et al., "Pressure frequency characteristics of the pericardial space and thorax during subxiphoid access for epicardial ventricular tachycardia ablation", Heart Rhythm 2010; 7:604-609.

Schuessler RB et al., "Animal studies of epicardial atrial ablation," Heart Rhythm, vol. 6, No. 12S, S41-S45 December Supplement 2009.

An International Search Report and a Written Opinion both dated Oct. 26, 2011, which issued during the prosecution of Applicant's PCT/IL11/00382.

An International Search Report and a Written Opinion both dated Sep. 17, 2012, which issued during the prosecution of Applicant's PCT/IL2012/000100.

An International Preliminary Report on Patentability dated Nov. 20, 2012, which issued during the prosecution of Applicant's PCT/IL11/00382.

An International Search Report dated Jul. 31, 2008, which issued during the prosecution of Applicant's PCT/US07/68818.

An Office Action dated Dec. 20, 2012, which issued during the prosecution of U.S. Appl. No. 11/653,115.

An Office Action dated Feb. 19, 2013, which issued during the prosecution of U.S. Appl. No. 13/010,555.

Fajardo et al., Effects of Hyperthermia in a Maligant Tumor, Cancer 45:613-623 (1980).

Short et al., Physical Hyperthermia and Cancer Therapy, Proceedings of the IEEE 68:133-142 (1980) p. 136, col. 2, para 6.

U.S. Appl. No. 60/370,190, filed Apr. 8, 2002.

U.S. Appl. No. 60/307,124, filed Jul. 23, 2001.

An Office Action dated May 17, 2013, which issued during the prosecution of U.S. Appl. No. 12/780,240.

An Invitation to pay additional fees dated Jun. 7, 2013, which issued during the prosecution of Applicant's PCT/IL2013/050134.

An International Search Report and a Written Opinion both dated Aug. 12, 2013 which issued during the prosecution of Applicant's PCT/IL2013/050134.

An International Search Report and a Written Opinion both dated Feb. 18, 2011 which issued during the prosecution of Applicant's PCT/IL2010/000683.

(56) References Cited

OTHER PUBLICATIONS

An International Preliminary Report of patentability dated Feb. 28, 2012 which issued during the prosecution of Applicant's PCT/IL2010/000683.
F. Mahfoud et al., Catherter-Based renal denervation increases insulin sensitivity and improves glucose metabolism. European Heart Journal 2010.
F. Mahfoud et al., Effects of Renal Sympathetic Denervation on Glucose Metabolism in Patients with Resistant Hypertension: A Pilot Study. Circulation 2011: 123 1940-1946.
Tai et al., Analysis of Nerve Conduction Including by Direct Current, J Comput Neuro. Published Online on 2009.
Ariav et al., Electrical Stimulation Induced Relaxation of Isolated Pig Aortas, Scientific Sessions 2011. American Heart Association. Abstract.
Stella et al., Cardiovascular Effects of Efferent renal nerve stimulation, Clin and Exper. Theory and Practice, 97-111, 1987.
Mortimer and Bhadra., Peripheral Nerve and Muscle Stimulation, Chapter 4.2, 1-48, 2004.
Stella et al., Effects of afferent renal nerve stimulation on renal hemodynamic and excretory functions, American Journal of physiology, 576-583, 1984.
Renal Sympathetic denervation in patients with treatment resistant hypertension, (1-7) Published online Nov. 2010.
Zhang et al., Mechanism of Nerve conduction Block induced by High-Frequency Biphasic Electrical Currents, IEEE Biomedical Engineering vol. 53 No. 12, 2006.
Bhadra et al., Reduction of the Onset Response in High-Frequency Nerve Block with Amplitude Ramps from Non-Zero Amplitudes, 650-653, 2009 IEEE.
Tai et al., Stimulation of Nerve Block by High-Frequency Sinusoidal Electrical Current Based on the Hodgkin-Huxley Model, IEEE Neural Systems and Rehabilitation engineering, vol. 13 No. 3, 2005.
Tsui, Electrical Nerve Stimulation, Springer Atlas of Ultrasound, pp. 9-18, 2008.
Bartus et al., Denervation (ablation) of Nerve Terminalis in renal arteries: early results of interventional treatment of arterial hypertension in Poland, Kardiologia Polska 2013, 71, 2: 152-158.
Krum et al., Catherter-Based Renal sympathetic denervation for resistant hypertension: A multicentre safety and proof-of-principle cohort study, Lancet 2009.
Chinushi M. et al., Blood pressure and autonomic responses to electrical stimulation of the renal arterial nerve before and after ablation of the renal artery, Pubmed, Hyper tension, Feb. 2013 61;(2) 450-6.
Wojakowski and Tendera, Renal sympathetic nerve in pathopysiology of resistant hypertension, European Society of Cardiology, downloaded on Jun. 2013.
Chinushi et al., Hemodynamic Responses and Histological Effects of Radiofrequency catheter Ablation to renal artery Sympathetic nerve. Abstract, downloaded on Jun. 2013.
Berjano, Biomedical Engineering Online Theoretical modeling for Radiofrequency Ablation: state-of-the-art and challenges for the future, published Apr. 2006.
Young and Henneman, Reversible block of nerve Conduction by Ultrasound, Archive of Neurology vol. 4, 1961.
Ballantine et al., Focal Destruction of nervous tissue by focused ultrasound : Biophysical factors influencing its Application, Medical Acoustics Research Group, 1956.
Colucci et al., Focused Ultrasound effects on nerve action potential in vitro, Department of Radiology, Harvard Medical Scholl, Ultrasound Med Biolog. 2009, 35(10); 1773-174.
Damianou, MRI Monitoring of the effects of tissue interfaces in the penetration of high intensity focused ultrasound in kidney in vivo, Ultrasound in Med & Bilo., vol. 30 No. 9, 2004.
Daum et al., In vivo Demonstration of noninvasive thermal surgery of the liver and kidney using an ultrasonic phase array, Ultrasound in Med & Bilo., vol. 25 No. 7, 1087-1098, 1999.
Foley et al., Image guided HIFU Neurolysis of peripheral nerve to treat Spasticity and Pain, Ultrasound in Med & Bilo., vol. 30 No. 9, 1199-1207, 2004.
Foley et al., Image guided High-Intensity focused Ultrasound for Condition block of peripheral nerves, Biomed Engineering, vol. 35 No. 1, 2007.
Zhang and Solomon, Nerve Ablation by high Intensity focused Ultrasound (HIFU) in swine model: Investigating HIFU as a non invasive Nerve block tool, WCIO 2011. Abstract.
Hynynen et al., Noninvasive arterial occlusion using MRI-Guided focused Ultrasound, Ultrasound in Med & Bilo., vol. 22 No. 8, 1071-1077, 1996.
Iwamoto et al., focused Ultrasound for Tactile Felling display, ICAT 2001.
Lele, Effects of Ultrasonic radiation on peripheral Nerve, with Observation on local Hearting, Experimental Neurology 8, 47-83, 1963.
Miharn et al., Temporally-Specific modification of Myelinated Axon excitability in vitro following a single ultrasound pulse,Ultrasound in Med & Bilo., 1990.
Rubin et al., Acute effects of Ultrasound on skeletal muscle oxygen tension , blood flow and capillary density, Ultrasound in Med & Bilo., vol. 16 No. 3, 271*277, 1990.
Renal sympathetic nerve ablation for Uncontrolled Hypertension, The New England journal of medicine, 932-934, 2009.
Wu et al., Preliminary Experience using high Intensity focused Ultrasound for the treatment of patient with advanced stage renal malignancy. The Journal of Urology, vol. 170, 2237-2240, 2003.
Young and Henneman, Functional Effects of focused Ultrasound on Mammalian nerves, Science New Series, vol. 134, No. 3489, 1961, 1521-1522.
Mizelle et al., Role of Renal nerve in Compensatory adaptation to chronic reduction in sodium intake, American Physiological Society, 1987.
Gibson, The Present Status of Renal Sympathectomy, California and Western Medicine, vol. 45, No. 1, 1936.
Kassab et al., Renal Denervation Attenuates the Sodium Retention and Hypertension Associated With Obesity, Hypertension, 1997. Abstract.
Winternitz et al., Role of the Renal Sympathetic Nerves in the Development and Maintenance of Hypertension in the Spontaneously Hypertensive Rat, J. Clin Invest 66(5), 1980. Abstract.
Augustyniak et al., Sympathetic overactivity as a cause of hypertension in chronic renal failure, Hypertension vol. 20, Issue 1, 2002. Abstract.
Brief introduction to bioimpedance (from www.ucl.ac.uk-medphys-research-eit).
Fletcher, Effect of episodic hypoxia on sympathetic activity and blood pressure, Respyration Pysiology, vol. 119, issue 2-3, 2000. Abstract.
Fletcher et al., Blood pressure response to chronic episodic hypoxia: the renin-angiotensin system, Journal of Applied physiology, 2001.
Illis, Spinal Cord Synapses in the Cat: The Reaction of the Boutons Termineaux at the Motoneurone Surface to Experimental Denervation, Brain a Journal of Neurology, vol. 87 issue 3, 1963, First page only.
Kopelman et al., Upper dorsal thoracoscopic sympathectomy for palmar hyperhidrosis. The use of harmonic scalpel versus diathermy. Ann Chir Gynaecol. 2001;90(3):203-5. Abstract.
Hashmonai et al., Thoracoscopic sympathectomy for palmar hyperhidrosis, Surgical Endoscopy May 2001, vol. 15, Issue 5, pp. 435-441.
Yoshimoto et al., Relationship between renal sympathetic nerve activity and renal blood flow during natural behavior in rats, American Journal of Physiology vol. 286, 2004.
DiBona. Dynamic Analysis of patterns of renal sympathetic nerve activity: Implications of renal functions, Exp Physiol. 90.2 pp. 159-161, 2004.
Valente et al., Laparoscopic renal denervation for intractable ADPKD-related pain, Nephrology Dialysis Transplantation vol. 6 issue 1, 2000.

(56) References Cited

OTHER PUBLICATIONS

An International Search Report and a Written Opinion both dated Aug. 11, 2015 which issued during of the prosecution of Applicant's PCT/IB2015/053350.
An International Preliminary Report on Patentability dated Nov. 8, 2016, which issued during the prosecution of Applicant's PCT/IB2015/053350.
An Advisory Action dated Aug. 8, 2016, which issued during the prosecution of U.S. Appl. No. 13/771,853.
European Search Report dated Jun. 7, 2016, which issued during the prosecution of Applicant's European App No. 13850508.6.
Schwarz et al;(2015) Autonomix presentation at TCT—Guidewire-Based Autonomic Neural Sensing From the Artery Lumen.
An International Search Report and a Written Opinion both dated Apr. 17, 2014 which issued during the prosecution of Applicant's PCT/IL2013/050903.
Luscher TF, Mahfoud F. Renal nerve ablation after symplicity htn-3: Confused at the higher level? Eur Heart J. 2014;35:1706-1711.
Lu (2015) Selective Proximal Renal Denervation Guided by Autonomic Responses Evoked via High-Frequency Stimulation in a Preclinical Canine Model.
Straub et al., 'A bacteria-induced switch of sympathetic effector mechanisms augments local inhibition of TNF-a and IL-6 secretion in the spleen' Jul. 2000 The FASEB Journal vol. 14 No. 10 1380-1388.
Gestel et al., 'Autonomic dysfunction in patients with chronic obstructive pulmonary disease (COPD)' J Thorac Dis 2010; 2:215-222.
Hering et al., 'Renal Denervation in Moderate to Severe CKD' J Am Soc Nephrol. [Jul. 2012]; 23(7): 1250-1257.
Jonson et al, 'Afferent electrical stimulation of mesenteric nerves inhibits duodenal HCO3 secretion via a spinal reflex activation of the splanchnic nerves in the rat' [1988] Acta Physiologica Scandinavica, 133: 545-550. doi: 10.1111/j.1748-1716.1988.tb08439.x.
Jonson et al., 'Splanchnic nerve stimulation inhibits duodenal HC03—secretion in the rat' Am J Physiol. [Dec. 1988];255 (6 Pt 1):G709-12.
Schwan, H.P. and Kay, C.F., 1956. Specific resistance of body tissues.*Circulation Research*, 4(6), pp. 664-670.
Kees et al., 'Via beta-adrenoceptors, stimulation of extrasplenic sympathetic nerve fibers inhibits lipopolysaccharideinduced TNF secretion in perfused rat spleen' J Neuroimmunol. Dec. 2003;145(1-2):77-85.
pcta.org, 'New (Dec. 6, 2013) Medtronic Multi-Electrode Renal Denervation Device Gets CE Mark and Australian Approval' http://www.ptca.org/news/2013/1206_MEDTRONIC_SYMPLICITY.html.
BusinessWire, 'St. Jude Medical Receives European Approval for New Renal Denervation System That Reduces Total Ablation Time by More Than 80 Percent' (Aug. 29, 2013) 2013 European Society of Cardiology.
mananatomy.com, 'Duodenum' http://www.mananatomy.com/digestive-system/duodenum.
Rosas-Ballina et al., 'Splenic nerve is required for cholinergic anti-inflammatory pathway control of TNF in endotoxemia' Aug. 5, 2008, vol. 105, No. 31 www.pnas.org/cgi/doi10.1073/pnas.0803237105.
Krum, H., et al. "Device-based antihypertensive therapy: therapeutic modulation of the autonomic nervous system." Circulation 123.2 (2011): 209.
Kilgore, Kevin L., et al. "Combined direct current and high frequency nerve block for elimination of the onset response." Engineering in Medicine and Biology Society, 2009. EMBC 2009. Annual International Conference of the IEEE. IEEE, 2009.
Bohm (2014) Symplicity HTN-3 trial_ what is it and what does it mean?
Ruilope (2014) Was there real denervation in the Symplicity HTN-3 trial.
Esler (2010) Renal sympathetic denervation in patients with treatment-resistant hypertension (The Symplicity HTN-2 Trial).
Renal Catheterization—SymplicityTM Renal Denervation System—downloaded from medtronicrdn.com Jun. 26, 2013.
An Office Action dated Mar. 11, 2016, which issued during the prosecution of U.S. Appl. No. 13/771,853.
Persu A, Jin Y, Fadl Elmula FE, Jacobs L, Renkin J, Kjeldsen S. Renal denervation after symplicity htn-3: An update.Curr Hypertens Rep. 2014;16:460.
Renal denervation and symplicity htn-3: "Dubium sapientiae initium" (doubt is the beginning of wisdom). Circ Res. 2014;115:211-214.
Patel HC, Hayward C, Di Mario C. Symplicity htn 3: The death knell for renal denervation in hypertension? Glob Cardiol Sci Pract. 2014;2014:94-98.
An Office Action dated Jan. 8, 2015, which issued during the prosecution of U.S. Appl. No. 13/771,853.
An International Preliminary Report on Patentability dated May 5, 2015, which issued during the prosecution of Applicant's PCT/IL2013/050903.
Changfeng (2009) Analysis of nerve conduction block induced by direct current.
Tsui (2008) Chapter 2 of Atlas of ultrasound and nerve stimulation guided regional anesthesia.
Changfeng (2005) Simulation of nerve block by high frequency sunusoidal electrical current.
Warchol-Celinska E, Januszewicz A, Prejbisz A, Kadziela J. Renal denervation after the symplicity htn-3 trial. Postepy Kardiol Interwencyjnej. 2014;10:75-77.
Calhoun DA, Jones D, Textor S, Goff DC, Murphy TP, Toto RD, White A, Cushman WC, White W, Sica D, Ferdinand K, Giles TD, Falkner B, Carey RM. Resistant hypertension: Diagnosis, evaluation, and treatment: A scientific statement from the American Heart Association professional education committee of the council for high blood pressure research Circulation. 2008.
Schlaich MP, Sobotka PA, Krum H, Whitbourn R, Walton A, Esler MD. Renal denervation as a therapeutic approach for hypertension: Novel implications for an old concept. Hypertension. 2009;54:1195-1201.
Esler MD, Bohm M, Sieved H, Rump CL, Schmieder RE, Krum H, Mahfoud F, Schlaich MP. Catheter-based renal denervation for treatment of patients with treatment-resistant hypertension: 36 month results from the Symplicity htn-2 randomized clinical trial. Eur Heart J. 2014;35:1752-1759.
"Blood pressure response to renal nerve stimulation in patients undergoing renal denervation: a feasibility study" , Gal et al., Journal of Human Hypertension (2014), 1-4, Macmillan Publishers Limited.
Sarafidis PA, Bakris GL. Resistant hypertension: An overview of evaluation and treatment. J Am Coll Cardiol. 2008;52:1749-1757.
Mahfoud F, Cremers B, Janker J, Link B, Vonend O, Ukena C, Linz D, Schmieder R, Rump LC, Kindermann I, Sobotka PA, Krum H, Scheller B, Schlaich M, Laufs U, Bohm M. Renal hemodynamics and renal function after catheter-based renal sympathetic denervation in patients with resistant hypertension. Hypertension. 2012;60:419-424.
Kjeldsen SE, Fadl Elmula FE, Persu A, Jin Y, Staessen JA. Renal sympathetic denervation in the aftermath of symplicity htn-Blood Press. 2014;23:256-261.
Kandzari DE, Bhatt DL, Sobotka PA, O'Neill WW, Esler M, Flack JM, Katzen BT, Leon MB, Massaro JM, Negoita M, Oparil S, Rocha-Singh K, Straley C, Townsend RR, Bakris G. Catheter-based renal denervation for resistant hypertension: Rationale and design of the symplicity htn-3 trial. Clin Cardiol. 2012;35:528-535.
U.S. Appl. No. 62/158,139, filed May 7, 2015.
Krum H, Schlaich MP, Sobotka PA, Bohm M, Mahfoud F, Rocha-Singh K, Katholi R, Esler MD. Percutaneous renal denervation in patients with treatment-resistant hypertension: Final 3-year report of the symplicity htn-1 study. Lancet. 2014;383:622-629.
Esler M. Illusions of truths in the symplicity htn-3 trial: Generic design strengths but neuroscience failings. J Am Soc Hypertens. 2014;8:593-598.
Schmieder RE. Hypertension: How should data from symplicity htn-3 be interpreted? Nat Rev Cardiol. 2014;11:375-376.
Pathak A, Ewen S, Fajadet J, Honton B, Mahfoud F, Marco J, Schlaich M, Schmieder R, Tsioufis K, Ukena C, Zeller T. From

(56) References Cited

OTHER PUBLICATIONS symplicity htn-3 to the renal denervation global registry: Where do we stand and where should we go? Eurointervention. 2014;10:21-23.

Pokushalov, Evgeny, et al. "A randomized comparison of pulmonary vein isolation with versus without concomitant renal artery denervation in patients with refractory symptomatic atrial fibrillation and resistant hypertension."*Journal of the American College of Cardiology* 60.13 (2012): 1163-1170.

Ruilope, L.M. and Arribas, F., 2014. Resistant Hypertension and Renal Denervation. Considerations on the Results of the Symplicity HTN-3 Trial.*Revista Española de Cardiología*, 67(11), pp. 881-882.

An Office Action dated Nov. 30, 2017, which issued during the prosecution of U.S. Appl. No. 14/794,737.

An Office Action dated Dec. 15, 2017, which issued during the prosecution of U.S. Appl. No. 14/795,529.

An International Search Report and a Written Opinion both dated Dec. 14, 2017, which issued during the prosecution of Applicant's PCT/IL2017/050967.

An International Search Report and a Written Opinion both dated Nov. 10, 2017, which issued during the prosecution of Applicant's PCT/IL2017/050533.

An International Search Report and a Written Opinion both dated May 24, 2017, which issued during the prosecution of Applicant's PCT/IL2017/050029.

An Invitation to pay additional fees dated Mar. 28, 2017, which issued during the prosecution of Applicant's PCT/IL2017/050029.

Notice of Allowance together with the English translation dated May 4, 2017 which issued during the prosecution of Chinese Patent Application No. 2013800692612.

An Office Action dated Jun. 15, 2017, which issued during the prosecution of U.S. Appl. No. 14/440,431.

An Invitation to pay additional fees dated Sep. 11, 2017, which issued during the prosecution of Applicant's PCT/IL2017/050533.

An Office Action dated Apr. 6, 2017, which issued during the prosecution of U.S. Appl. No. 13/771,853.

European Search Report dated May 9, 2017, which issued during the prosecution of Applicant's European App No. 16203956.4.

An English translation of an Office Action dated Nov. 18, 2016, which issued during the prosecution of Chinese Patent Application No. 201380069261.2.

An Office Action dated Sep. 6, 2018, which issued during the prosecution of U.S. Appl. No. 15/001,615.

An Office Action dated May 15, 2018, which issued during the prosecution of U.S. Appl. No. 14/972,756.

An International Search Report and a Written Opinion both dated Jun. 11, 2018, which issued during the prosecution of Applicant's PCT/IL2018/050231.

An Office Action dated Feb. 21, 2019, which issued during the prosecution of U.S. Appl. No. 15/330,790.

* cited by examiner

| # | NAME | UNITS | DEFINITION | INTERPRETATION | INCLUSION/EXCLUSION RATIONALE |
|---|---|---|---|---|---|
| 1 | $dP/dT_{max}$ | mmHg/sec | Maximal derivative (dP/dT) of arterial pressure wave during systolic upstroke. See Fig. 2 | Directly associated with LV contractility, hardly affected by counter mechanisms (except for HR). Indicates for: $\beta_1 \to \Uparrow$, $\alpha_2 \to \sim\Downarrow$, $\alpha_1 \to \Downarrow\Uparrow$ | Single mechanism parameter. Responsive in large and small effects. Responds most quickly to allow online efficient procedure. |
| 2 | Skewness($\mu_3$) | $mmHg^3$ (power of 3) | Third moment of the blood pressure wave. $$\mu_3 = E\left[\left(\frac{BP-\mu}{\sigma}\right)^3\right]$$ $\sigma$ – standard deviation of BP $\mu$ – average of BP E – averaging operator (expected value) | Waveform parameter, without direct physiological meaning. Increased skewness means that pressure wave is shifted towards higher energy during systole and implies greater vascular stiffness. See Fig. 4 | Very responsive, mostly to slow RAS effects. |
| 3 | HR | BPM (1/min) | The number of detected beats within a minute. Defined as 60/T, where T is the instantaneous heart period (see Fig. 2) | Directly represents the cardiac chronotropic function of the autonomic system | Not always responsive, but required for chronotropic effect and for safety of stimulation |

FIG. 1A

| # | NAME | UNITS | DEFINITION | INTERPRETATION | INCLUSION/EXCLUSION RATIONALE |
|---|------|-------|------------|----------------|-------------------------------|
| 4 | Augmentation Index (AIx) | % | Augmentation index of pressure as a result of reflected wave from periphery. Defined as the ratio between irregular pressure waveform amplitude and total pulse pressure. See Fig. 3 for graphical description. | Strongly associated with arterial stiffness and peripheral resistance. Increases with reduced compliance and elevated peripheral resistance. | Medium responses observed, both fast and slow dynamics. Has wide physiological meaning and therefore desired. |
| 5 | Diastolic decay time constant (D$\tau$) | Sec | Exponential pressure decay constant time (RC) during diastolic period. Calculated through curve fitting of the diastolic pressure (See Fig. 2.) to an exponential function of the form: $A \cdot e^{-t/\tau}$, where A is an arbitrary factor and $\tau$ is the extracted parameter. | Associated with total peripheral resistance (R) and arterial compliance (C). When sympathetic tone increases, may show lower net effect because of R increase with C decrease. | Medium response level, but has significant physiological meaning and allows estimation of total peripheral resistance (while knowing the compliance response) |
| 6 | Diastolic Average Slope (Dslope) | mmHg/sec | Average of the pressure derivative during diastolic phase | Same interpretation as D$\tau$ | Responsive, but correlated to D$\tau$. Did identify very low responses and therefore seems useful. |

FIG. 1B

| # | NAME | UNITS | DEFINITION | INTERPRETATION | INCLUSION/EXCLUSION RATIONALE |
|---|------|-------|------------|----------------|-------------------------------|
| 7 | SP | mmHg | Maximal pressure point of the pressure wave (see Fig. 2-SAP) | Uses as clinical marker for increased stiffness and increased contractility, but is highly influenced from other mechanisms, including preload | Important to act as fiducial blood pressure information, and identify trends by its relationship with other parameters |
| 8 | Systolic Average Slope (Sslope) | mmHg/sec | Average of the pressure derivative during systolic phase | Represents the contractility of the heart (inotropic effect) but is also determined by the augmentation index, HR and systolic duration ratio, unlike the dP/dTmax. | Responsive, but not enough physiological interpretation Correlates to dP/dT and therefore not needed |
| 9 | Pulse Pressure (PP) | mmHg | Difference between systolic pressure (maximal pressure) and diastolic pressure (minimal pressure). PP = SP−DP | Clinically used to assess arterial stiffness, but is influenced by all cardiovascular mechanisms. | Not responsive enough, balanced by RAS influences |
| 10 | Systolic Duration Ratio (SDR) | % | Systolic duration ratio: Tsys/Tperiod. See Fig. 2. | May indicate a dromotropic effect, changing atrio-ventricular delay, which acts through activation of left cardiac vagal nerve, unlike chronotropc effect. Influenced by heart rate and therefore may need a correction to given heart rate. | Not responsive enough, and not useful as classifier (per given data set). Dromotropy can be typified through ECG signal. |

FIG. 1C

TECHNIQUES FOR USE WITH NERVE TISSUE

CROSS-REFERENCES TO RELATED APPLICATIONS

The present application claims the benefit of U.S. Provisional Application 62/158,139 to Gross et al., filed May 7, 2015, and entitled "Techniques for use with nerve tissue," which is incorporated herein by reference.

BACKGROUND

Hypertension is a prevalent condition in the general population, particularly in older individuals. Sympathetic nervous pathways, such as those involving the renal nerve, are known to play a role in regulating blood pressure. Ablation of renal nerve tissue from the renal artery is a known technique for treating hypertension.

SUMMARY OF THE INVENTION

Techniques are described for using blood pressure parameters, derived from arterial blood pressure waveforms, to facilitate (i) selecting a subject for renal nerve ablation, (ii) defining more specifically a condition (e.g., a pathology) of the subject, (iii) locating target ablation sites within a renal artery of the subject, (iv) deciding on a modality of ablation energy to be used, and/or (v) monitoring the progress and/or success of an ablation procedure.

For some applications the techniques described are performed generally manually, e.g., by a physician. For some applications the techniques described are at least partly automated, e.g., using a device comprising a control unit, a transluminally-advanceable longitudinal member such as a catheter, and one or more electrodes at a distal portion of the longitudinal member.

There is therefore provided, in accordance with an application of the present invention, a method, including:
applying an excitatory current to renal nerve fibers of a subject;
determining a change in a parameter of the subject in response to the excitatory current, the parameter being a fastest rate of increase in arterial pressure during a systolic upstroke of an arterial pressure wave of the subject;
in response to the change, deciding whether to ablate the renal nerve fibers; and
in response to the deciding, applying ablation energy to the renal nerve fibers.

In an application:
applying the excitatory current includes applying the excitatory current to renal nerve fibers proximate to a first location of a renal artery wall,
deciding whether to ablate the renal nerve fibers includes deciding whether to ablate the renal nerve fibers proximate to the first location, and
the method further includes:
applying the excitatory current to renal nerve fibers proximate to a second location of a renal artery wall;
determining a second change in the parameter in response to the excitatory current applied to the renal nerve fibers proximate to the second location; and
in response to the second change, deciding whether to ablate the renal nerve fibers proximate to the second location.

There is further provided, in accordance with an application of the present invention, a method, including:

measuring a first value of a parameter of a subject while the subject is at rest, the parameter being a fastest rate of increase in arterial pressure during a systolic upstroke of an arterial pressure wave of the subject;
applying an excitatory current to renal nerve fibers of a subject;
while applying the excitatory current, measuring a second value of the parameter;
in response to a difference between the first value and the second value, deciding whether to ablate the renal nerve fibers; and
in response to the deciding, applying ablation energy to the renal nerve fibers.

There is further provided, in accordance with an application of the present invention, a method, including:
applying an excitatory current to renal nerve fibers of a subject;
determining a change in a parameter of the subject in response to the excitatory current, the parameter being a fastest rate of increase in arterial pressure during a systolic upstroke of an arterial pressure wave of the subject;
in response to the change, selecting an ablation modality from a plurality of ablation modalities; and
in response to the selecting, ablating the renal nerve fibers using the selected ablation modality.

There is further provided, in accordance with an application of the present invention, a method, including:
applying a first application of excitatory current to renal nerve fibers of a subject;
determining a first change in a parameter of the subject in response to the first application of excitatory current, the parameter being a fastest rate of increase in arterial pressure during a systolic upstroke of an arterial pressure wave of the subject;
subsequently, applying a first application of ablating energy to the renal nerve fibers;
subsequently, applying a second application of excitatory current to renal nerve fibers of a subject;
determining a second change in the parameter in response to the second application of excitatory current;
determining a difference between the first change and the second change;
deciding whether to apply a second application of ablation energy to the renal nerve fibers; and
in response to the deciding, applying the second application of ablation energy to the renal nerve fibers.

There is further provided, in accordance with an application of the present invention, a method, including:
transluminally advancing a distal portion of a longitudinal member of a device into a renal artery of a subject;
operating the device to drive an electrode disposed on the distal portion of the longitudinal member to apply an excitatory current to nerve tissue of the renal artery;
receiving (i) a first value, the first value being indicative of a parameter of the subject before a start of the application of the current, and (ii) a second value, the second value being indicative of the parameter of the subject after a start of the application of the current, the parameter being a fastest rate of increase in arterial pressure during a systolic upstroke of an arterial pressure wave of the subject;
determining if a difference between the first value and the second value is smaller than a threshold difference; and
in response to the determining:
only if the determined difference is smaller than the threshold difference, withdrawing the longitudinal member from the subject without having applied ablation energy to the renal artery.

There is further provided, in accordance with an application of the present invention, apparatus including:
a transluminal electrode catheter, including:
a flexible shaft, dimensioned for advancement of a distal portion of the shaft into a renal artery of a subject;
a plurality of electrodes disposed at the distal portion of the shaft; and
an arterial blood pressure sensor; and
a control unit, electrically coupled to the catheter, and configured to:
use the sensor to measure a first value of a parameter of the subject while the subject is at rest, the parameter being a fastest rate of increase in arterial pressure during a systolic upstroke of an arterial pressure wave of the subject,
drive at least one of the electrodes to apply an excitatory current to renal nerve fibers of the subject,
while applying the excitatory current, use the blood pressure sensor to measure a second value of the parameter,
determine if a difference between the first value and the second value is greater than a threshold difference, and
in response to the determining:
only if the determined difference is greater than the threshold difference, enable an ablation function of the control unit.

There is further provided, in accordance with an application of the present invention, a method, including:
applying an excitatory current to renal nerve fibers of a subject;
determining a change in a parameter of the subject in response to the excitatory current, the parameter of the subject being a skewness of an arterial pressure wave of the subject;
in response to the change, deciding whether to ablate the renal nerve fibers; and
in response to the deciding, applying ablation energy to the renal nerve fibers.

In an application:
applying the excitatory current includes applying the excitatory current to renal nerve fibers proximate to a first location of a renal artery wall,
deciding whether to ablate the renal nerve fibers includes deciding whether to ablate the renal nerve fibers proximate to the first location, and
the method further includes:
applying the excitatory current to renal nerve fibers proximate to a second location of a renal artery wall;
determining a second change in the parameter in response to the excitatory current applied to the renal nerve fibers proximate to the second location; and
in response to the second change, deciding whether to ablate the renal nerve fibers proximate to the second location.

There is further provided, in accordance with an application of the present invention, a method, including:
measuring a first value of a parameter of a subject while the subject is at rest, the parameter being skewness of an arterial pressure wave of the subject;
applying an excitatory current to renal nerve fibers of a subject;
while applying the excitatory current, measuring a second value of the parameter;
in response to a difference between the first value and the second value, deciding whether to ablate the renal nerve fibers; and
in response to the deciding, applying ablation energy to the renal nerve fibers.

There is further provided, in accordance with an application of the present invention, a method, including:
applying an excitatory current to renal nerve fibers of a subject;
determining a change in a parameter of the subject in response to the excitatory current, the parameter of the subject being skewness of an arterial pressure wave of the subject;
in response to the change, selecting an ablation modality from a plurality of ablation modalities; and
in response to the selecting, ablating the renal nerve fibers using the selected ablation modality.

There is further provided, in accordance with an application of the present invention, a method, including:
applying a first application of excitatory current to renal nerve fibers of a subject;
determining a first change in a parameter of the subject in response to the first application of excitatory current, the parameter of the subject being skewness of an arterial pressure wave of the subject;
subsequently, applying a first application of ablating energy to the renal nerve fibers;
subsequently, applying a second application of excitatory current to renal nerve fibers of a subject;
determining a second change in the parameter in response to the second application of excitatory current;
determining a difference between the first change and the second change;
deciding whether to apply a second application of ablation energy to the renal nerve fibers; and
in response to the deciding, applying the second application of ablation energy to the renal nerve fibers.

There is further provided, in accordance with an application of the present invention, a method, including:
transluminally advancing a distal portion of a longitudinal member of a device into a renal artery of a subject;
operating the device to drive an electrode disposed on the distal portion of the longitudinal member to apply an excitatory current to nerve tissue of the renal artery;
receiving (i) a first value, the first value being indicative of a parameter of the subject before a start of the application of the current, and (ii) a second value, the second value being indicative of the parameter of the subject after a start of the application of the current, the parameter being skewness of an arterial pressure wave of the subject;
determining if a difference between the first value and the second value is smaller than a threshold difference; and
in response to the determining:
only if the determined difference is smaller than the threshold difference, withdrawing the longitudinal member from the subject without having applied ablation energy to the renal artery.

There is further provided, in accordance with an application of the present invention, apparatus including:
a transluminal electrode catheter, including:
a flexible shaft, dimensioned for advancement of a distal portion of the shaft into a renal artery of a subject;
a plurality of electrodes disposed at the distal portion of the shaft; and
an arterial blood pressure sensor; and
a control unit, electrically coupled to the catheter, and configured to:

use the sensor to measure a first value of a parameter of the subject while the subject is at rest, the parameter being skewness of an arterial pressure wave of the subject, drive at least one of the electrodes to apply an excitatory current to renal nerve fibers of the subject, while applying the excitatory current, use the blood pressure sensor to measure a second value of the parameter, determine if a difference between the first value and the second value is greater than a threshold difference, and in response to the determining:
only if the determined difference is greater than the threshold difference, enable an ablation function of the control unit.

There is further provided, in accordance with an application of the present invention, a method, including:

applying an excitatory current to renal nerve fibers of a subject;

determining a change in a parameter of the subject in response to the excitatory current, the parameter of the subject being a heart rate of the subject;

in response to the change, deciding whether to ablate the renal nerve fibers; and in response to the deciding, applying ablation energy to the renal nerve fibers.

In an application:

applying the excitatory current includes applying the excitatory current to renal nerve fibers proximate to a first location of a renal artery wall, deciding whether to ablate the renal nerve fibers includes deciding whether to ablate the renal nerve fibers proximate to the first location, and the method further includes:
applying the excitatory current to renal nerve fibers proximate to a second location of a renal artery wall;

determining a second change in the parameter in response to the excitatory current applied to the renal nerve fibers proximate to the second location; and in response to the second change, deciding whether to ablate the renal nerve fibers proximate to the second location.

There is further provided, in accordance with an application of the present invention, a method, including:

measuring a first value of a parameter of a subject while the subject is at rest, the parameter being a heart rate of the subject;

applying an excitatory current to renal nerve fibers of a subject;

while applying the excitatory current, measuring a second value of the parameter;

in response to a difference between the first value and the second value, deciding whether to ablate the renal nerve fibers; and in response to the deciding, applying ablation energy to the renal nerve fibers.

There is further provided, in accordance with an application of the present invention, a method, including:

applying an excitatory current to renal nerve fibers of a subject;

determining a change in a parameter of the subject in response to the excitatory current, the parameter of the subject being a heart rate of the subject;

in response to the change, selecting an ablation modality from a plurality of ablation modalities; and in response to the selecting, ablating the renal nerve fibers using the selected ablation modality.

There is further provided, in accordance with an application of the present invention, a method, including:

applying a first application of excitatory current to renal nerve fibers of a subject;

determining a first change in a parameter of the subject in response to the first application of excitatory current, the parameter of the subject being a heart rate of the subject;

subsequently, applying a first application of ablating energy to the renal nerve fibers;

subsequently, applying a second application of excitatory current to renal nerve fibers of a subject;

determining a second change in the parameter in response to the second application of excitatory current;

determining a difference between the first change and the second change;

deciding whether to apply a second application of ablation energy to the renal nerve fibers; and in response to the deciding, applying the second application of ablation energy to the renal nerve fibers.

There is further provided, in accordance with an application of the present invention, a method, including:

transluminally advancing a distal portion of a longitudinal member of a device into a renal artery of a subject;

operating the device to drive an electrode disposed on the distal portion of the longitudinal member to apply an excitatory current to nerve tissue of the renal artery;

receiving (i) a first value, the first value being indicative of a parameter of the subject before a start of the application of the current, and (ii) a second value, the second value being indicative of the parameter of the subject after a start of the application of the current, the parameter being a heart rate of the subject;

determining if a difference between the first value and the second value is smaller than a threshold difference; and in response to the determining:
only if the determined difference is smaller than the threshold difference, withdrawing the longitudinal member from the subject without having applied ablation energy to the renal artery.

There is further provided, in accordance with an application of the present invention, apparatus including:

a transluminal electrode catheter, including:
a flexible shaft, dimensioned for advancement of a distal portion of the shaft into a renal artery of a subject;
a plurality of electrodes disposed at the distal portion of the shaft; and
an arterial blood pressure sensor; and
a control unit, electrically coupled to the catheter, and configured to:
use the sensor to measure a first value of a parameter of the subject while the subject is at rest, the parameter being a heart rate of the subject,
drive at least one of the electrodes to apply an excitatory current to renal nerve fibers of the subject,
while applying the excitatory current, use the blood pressure sensor to measure a second value of the parameter,
determine if a difference between the first value and the second value is greater than a threshold difference, and
in response to the determining:
only if the determined difference is greater than the threshold difference, enable an ablation function of the control unit.

There is further provided, in accordance with an application of the present invention, a method, including:

applying an excitatory current to renal nerve fibers of a subject;

determining a change in a parameter of the subject in response to the excitatory current, the parameter of the subject being an augmentation index of an arterial pressure wave of the subject;

in response to the change, deciding whether to ablate the renal nerve fibers; and in response to the deciding, applying ablation energy to the renal nerve fibers.

In an application:

applying the excitatory current includes applying the excitatory current to renal nerve fibers proximate to a first location of a renal artery wall, deciding whether to ablate the renal nerve fibers includes deciding whether to ablate the renal nerve fibers proximate to the first location, and the method further includes:

applying the excitatory current to renal nerve fibers proximate to a second location of a renal artery wall;

determining a second change in the parameter in response to the excitatory current applied to the renal nerve fibers proximate to the second location; and in response to the second change, deciding whether to ablate the renal nerve fibers proximate to the second location.

There is further provided, in accordance with an application of the present invention, a method, including:

measuring a first value of a parameter of a subject while the subject is at rest, the parameter being an augmentation index of an arterial pressure wave of the subject;

applying an excitatory current to renal nerve fibers of a subject;

while applying the excitatory current, measuring a second value of the parameter;

in response to a difference between the first value and the second value, deciding whether to ablate the renal nerve fibers; and in response to the deciding, applying ablation energy to the renal nerve fibers.

There is further provided, in accordance with an application of the present invention, a method, including:

applying an excitatory current to renal nerve fibers of a subject;

determining a change in a parameter of the subject in response to the excitatory current, the parameter of the subject being an augmentation index of an arterial pressure wave of the subject;

in response to the change, selecting an ablation modality from a plurality of ablation modalities; and in response to the selecting, ablating the renal nerve fibers using the selected ablation modality.

There is further provided, in accordance with an application of the present invention, a method, including:

applying a first application of excitatory current to renal nerve fibers of a subject;

determining a first change in a parameter of the subject in response to the first application of excitatory current, the parameter of the subject being an augmentation index of an arterial pressure wave of the subject;

subsequently, applying a first application of ablating energy to the renal nerve fibers;

subsequently, applying a second application of excitatory current to renal nerve fibers of a subject;

determining a second change in the parameter in response to the second application of excitatory current;

determining a difference between the first change and the second change;

deciding whether to apply a second application of ablation energy to the renal nerve fibers; and in response to the deciding, applying the second application of ablation energy to the renal nerve fibers.

There is further provided, in accordance with an application of the present invention, a method, including:

transluminally advancing a distal portion of a longitudinal member of a device into a renal artery of a subject;

operating the device to drive an electrode disposed on the distal portion of the longitudinal member to apply an excitatory current to nerve tissue of the renal artery;

receiving (i) a first value, the first value being indicative of a parameter of the subject before a start of the application of the current, and (ii) a second value, the second value being indicative of the parameter of the subject after a start of the application of the current, the parameter being an augmentation index of an arterial pressure wave of the subject;

determining if a difference between the first value and the second value is smaller than a threshold difference; and in response to the determining:

only if the determined difference is smaller than the threshold difference, withdrawing the longitudinal member from the subject without having applied ablation energy to the renal artery.

There is further provided, in accordance with an application of the present invention, apparatus including:

a transluminal electrode catheter, including:

a flexible shaft, dimensioned for advancement of a distal portion of the shaft into a renal artery of a subject;

a plurality of electrodes disposed at the distal portion of the shaft; and an arterial blood pressure sensor; and a control unit, electrically coupled to the catheter, and configured to:

use the sensor to measure a first value of a parameter of the subject while the subject is at rest, the parameter being an augmentation index of an arterial pressure wave of the subject, drive at least one of the electrodes to apply an excitatory current to renal nerve fibers of the subject, while applying the excitatory current, use the blood pressure sensor to measure a second value of the parameter, determine if a difference between the first value and the second value is greater than a threshold difference, and in response to the determining:

only if the determined difference is greater than the threshold difference, enable an ablation function of the control unit.

There is further provided, in accordance with an application of the present invention, a method, including:

applying an excitatory current to renal nerve fibers of a subject;

determining a change in a parameter of the subject in response to the excitatory current, the parameter of the subject being a diastolic decay time constant of an arterial pressure wave of the subject;

in response to the change, deciding whether to ablate the renal nerve fibers; and in response to the deciding, applying ablation energy to the renal nerve fibers.

In an application:

applying the excitatory current includes applying the excitatory current to renal nerve fibers proximate to a first location of a renal artery wall, deciding whether to ablate the renal nerve fibers includes deciding whether to ablate the renal nerve fibers proximate to the first location, and the method further includes:
applying the excitatory current to renal nerve fibers proximate to a second location of a renal artery wall;
determining a second change in the parameter in response to the excitatory current applied to the renal nerve fibers proximate to the second location; and
in response to the second change, deciding whether to ablate the renal nerve fibers proximate to the second location.

There is further provided, in accordance with an application of the present invention, a method, including:
measuring a first value of a parameter of a subject while the subject is at rest, the parameter being a diastolic decay time constant of an arterial pressure wave of the subject;
applying an excitatory current to renal nerve fibers of a subject;
while applying the excitatory current, measuring a second value of the parameter;
in response to a difference between the first value and the second value, deciding whether to ablate the renal nerve fibers; and
in response to the deciding, applying ablation energy to the renal nerve fibers.

There is further provided, in accordance with an application of the present invention, a method, including:
applying an excitatory current to renal nerve fibers of a subject;
determining a change in a parameter of the subject in response to the excitatory current, the parameter of the subject being a diastolic decay time constant of an arterial pressure wave of the subject;
in response to the change, selecting an ablation modality from a plurality of ablation modalities; and
in response to the selecting, ablating the renal nerve fibers using the selected ablation modality.

There is further provided, in accordance with an application of the present invention, a method, including:
applying a first application of excitatory current to renal nerve fibers of a subject;
determining a first change in a parameter of the subject in response to the first application of excitatory current, the parameter of the subject being a diastolic decay time constant of an arterial pressure wave of the subject;
subsequently, applying a first application of ablating energy to the renal nerve fibers;
subsequently, applying a second application of excitatory current to renal nerve fibers of a subject;
determining a second change in the parameter in response to the second application of excitatory current;
determining a difference between the first change and the second change;
deciding whether to apply a second application of ablation energy to the renal nerve fibers; and
in response to the deciding, applying the second application of ablation energy to the renal nerve fibers.

There is further provided, in accordance with an application of the present invention, a method, including:
transluminally advancing a distal portion of a longitudinal member of a device into a renal artery of a subject;
operating the device to drive an electrode disposed on the distal portion of the longitudinal member to apply an excitatory current to nerve tissue of the renal artery;
receiving (i) a first value, the first value being indicative of a parameter of the subject before a start of the application of the current, and (ii) a second value, the second value being indicative of the parameter of the subject after a start of the application of the current, the parameter being a diastolic decay time constant of an arterial pressure wave of the subject;
determining if a difference between the first value and the second value is smaller than a threshold difference; and
in response to the determining:
only if the determined difference is smaller than the threshold difference, withdrawing the longitudinal member from the subject without having applied ablation energy to the renal artery.

There is further provided, in accordance with an application of the present invention, apparatus including:
a transluminal electrode catheter, including:
a flexible shaft, dimensioned for advancement of a distal portion of the shaft into a renal artery of a subject;
a plurality of electrodes disposed at the distal portion of the shaft; and
an arterial blood pressure sensor; and
a control unit, electrically coupled to the catheter, and configured to:
use the sensor to measure a first value of a parameter of the subject while the subject is at rest, the parameter being a diastolic decay time constant of an arterial pressure wave of the subject,
drive at least one of the electrodes to apply an excitatory current to renal nerve fibers of the subject,
while applying the excitatory current, use the blood pressure sensor to measure a second value of the parameter,
determine if a difference between the first value and the second value is greater than a threshold difference, and
in response to the determining:
only if the determined difference is greater than the threshold difference, enable an ablation function of the control unit.

There is further provided, in accordance with an application of the present invention, a method, including:
transluminally advancing an electrode into a renal artery of a subject;
while the subject is at rest, measuring a first value of a first parameter and a first value of a second parameter, the first parameter and the second parameter selected from the group consisting of: (i) a fastest rate of increase in arterial pressure during a systolic upstroke of an arterial pressure wave of the subject, (ii) a skewness of the arterial pressure wave of the subject, (iii) a heart rate of the subject, (iv) an augmentation index of the arterial pressure wave of the subject, and (v) a diastolic decay constant of the arterial pressure wave of the subject;
applying an excitatory current to renal nerve fibers of a subject;
while applying the excitatory current, measuring a second value of the first parameter and a second value of the second parameter;
determining (i) a first difference between the first value of the first parameter and the second value of the first parameter, and (ii) a second difference between the first value of the second parameter and the second value of the second parameter; and
in response to the first difference and the second difference, diagnosing a pathology of the subject.

In an application, the method further includes:
while the subject is at rest, measuring a first value of a third parameter selected from the group;

while applying the excitatory current, measuring a second value of the third parameter; and determining a third difference between the first value of the third parameter and the second value of the third parameter, and diagnosing the pathology in response includes diagnosing the pathology in response to the first difference, the second difference, and the third difference.

In an application, the method further includes:

while the subject is at rest, measuring a first value of a fourth parameter selected from the group;

while applying the excitatory current, measuring a second value of the fourth parameter; and determining a fourth difference between the first value of the fourth parameter and the second value of the fourth parameter, and diagnosing the pathology in response includes diagnosing the pathology in response to the first difference, the second difference, the third difference, and the fourth difference.

In an application, the method further includes:

while the subject is at rest, measuring a first value of a fifth parameter selected from the group;

while applying the excitatory current, measuring a second value of the fifth parameter; and determining a fifth difference between the first value of the fifth parameter and the second value of the fifth parameter, and diagnosing the pathology in response includes diagnosing the pathology in response to the first difference, the second difference, the third difference, the fourth difference, and the fifth difference.

The present invention will be more fully understood from the following detailed description of applications thereof, taken together with the drawings, in which:

BRIEF DESCRIPTION OF THE DRAWINGS

FIGS. 1A, 1B, and 1C show a table of evaluated parameters, which spans across FIGS. 1A, 1B, and 1C, in accordance with some applications of the invention;

DETAILED DESCRIPTION OF EMBODIMENTS

Figure 2:
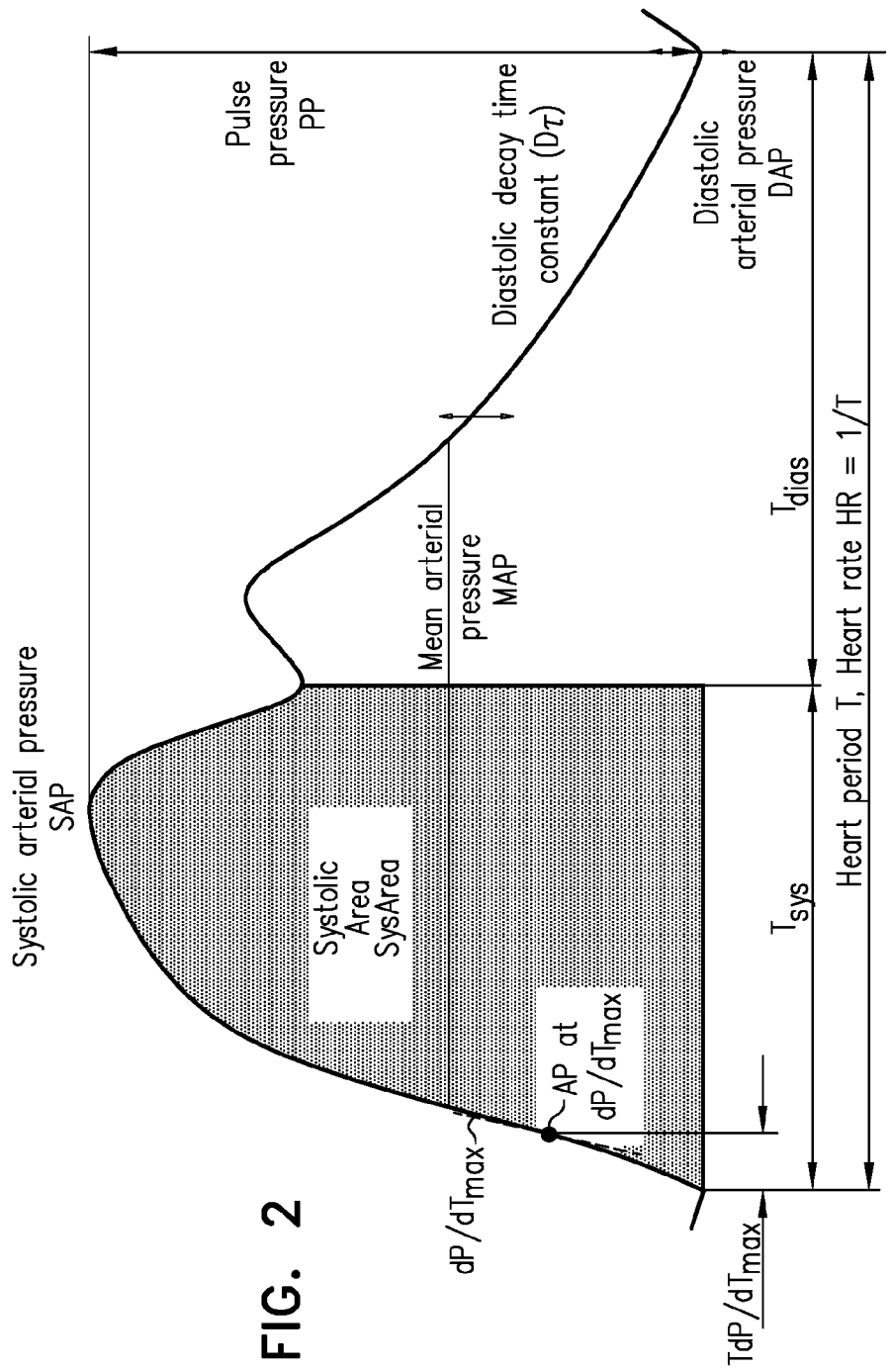
FIGS. 2, 3, and 4 are schematic illustrations showing arterial pressure waves, with annotations explaining some of the parameters of FIGS. 1A, 1B, and 1C, in accordance with some applications of the invention.
Figure 3:
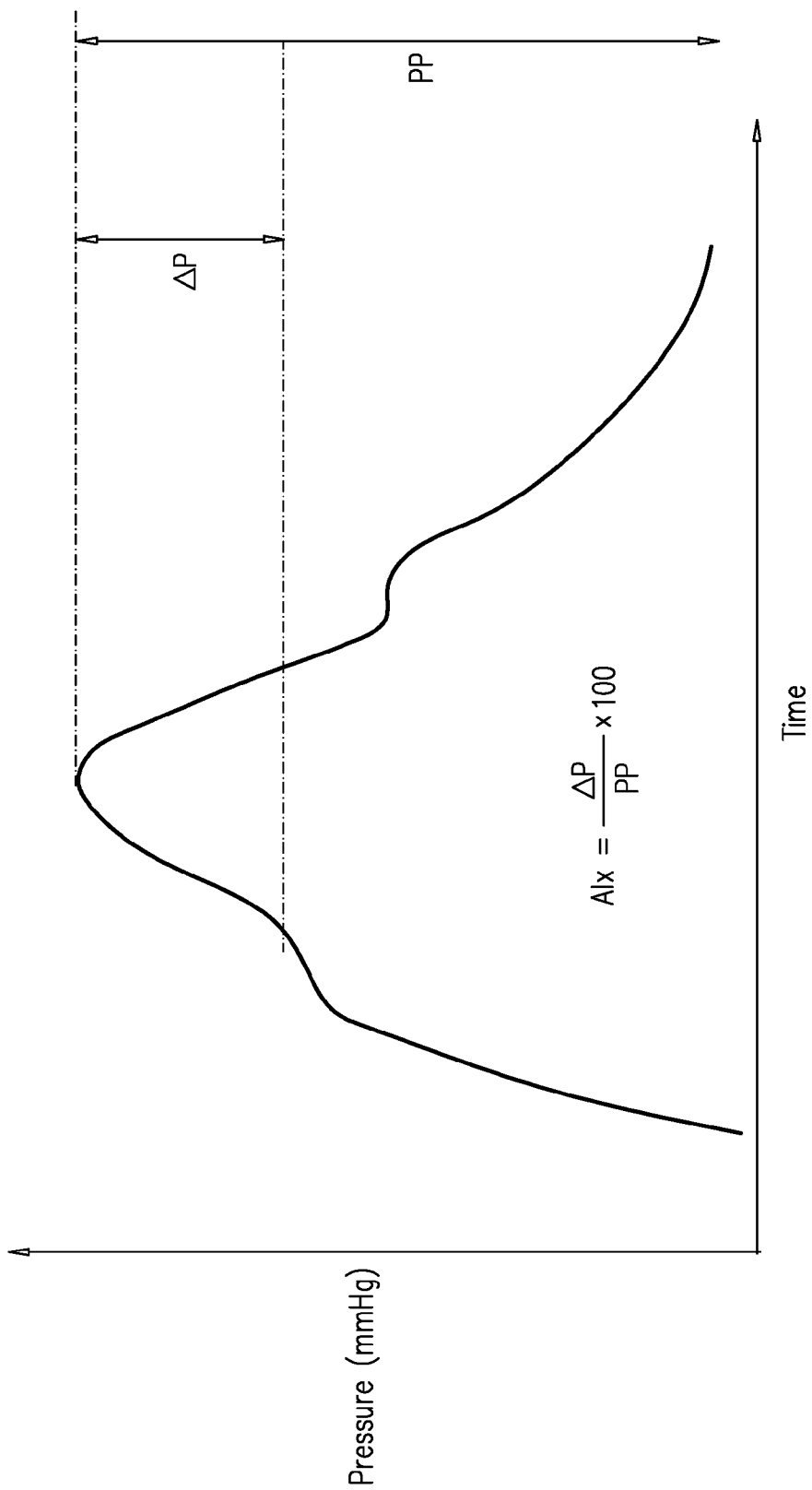
Figure 4:
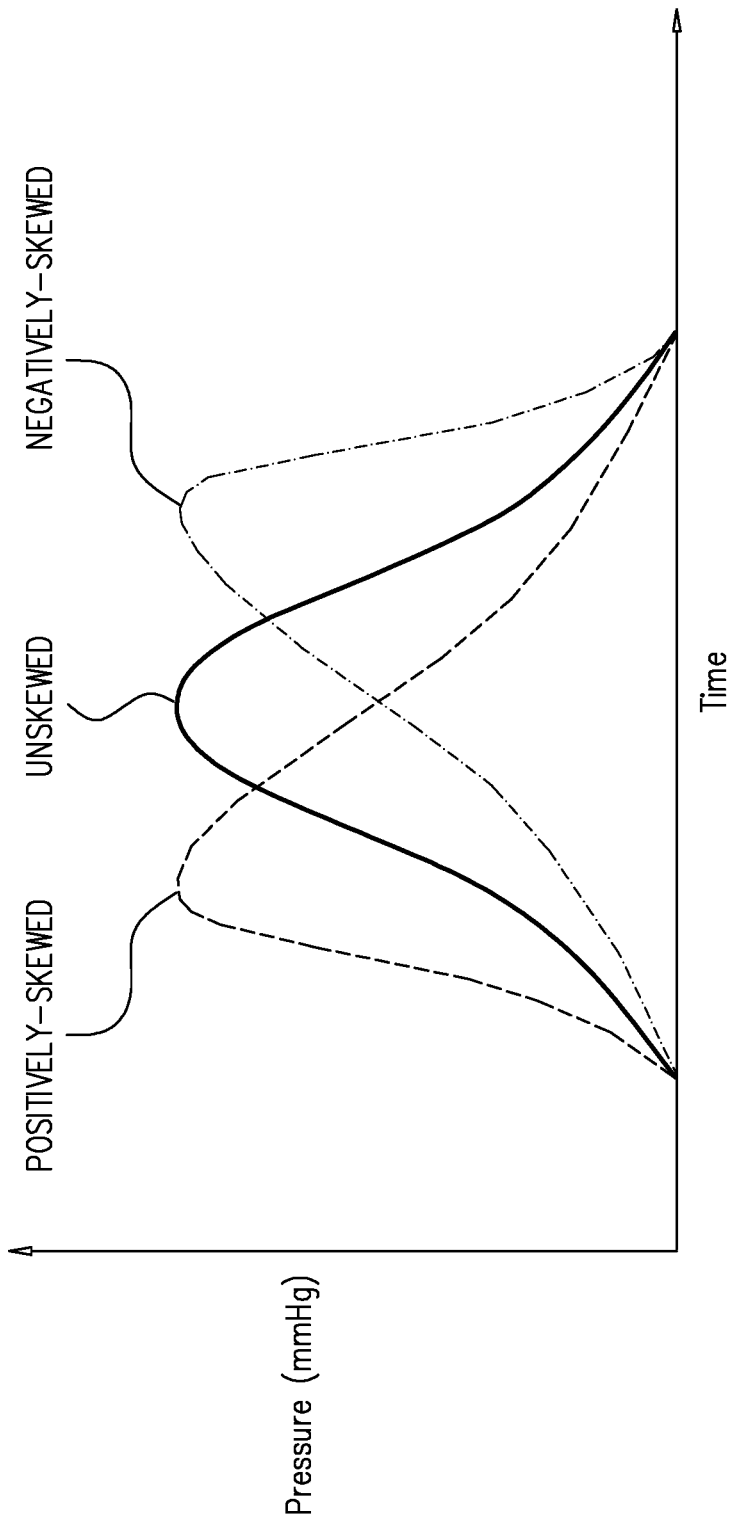

Reference is made to FIGS. 1A-C, 2, 3, and 4. FIGS. 1A-C show a table of evaluated parameters, which spans across FIGS. 1A-C, in accordance with some applications of the invention. FIGS. 2, 3, and 4 are schematic illustrations showing arterial pressure waves, with annotations explaining some of the parameters of FIGS. 1A-C, in accordance with some applications of the invention.

Experiments were performed in a porcine model. Arterial blood pressure was monitored before, during, and after excitation of (i.e., induction of action potentials in) a renal nerve. Various parameters derived from the resulting trace were evaluated, in order to determine which respond clearly (e.g., a quantitatively large change) and reliably (e.g., qualitatively similarities in changes between animals, such as changing in the same direction in each animal) to renal nerve excitation.

The evaluated parameters were ranked according to the results of the experiments; the top ten parameters appear in the table that spans FIGS. 1A-C.

dP/dT_max is the maximal derivative (dP/dT) of the pressure wave during systolic upstroke (i.e., the fastest rate of increase in arterial pressure during the systolic upstroke). (In the interpretations column, beta_1, alpha_2, and alpha_1 refer to subtypes of adrenergic receptor.) dP/dT_max is illustrated in FIG. 2. FIG. 2 also shows (i) the parameter TdP/dT_max, which is the time to reach dP/dT_max, and (ii) the parameter AP at dP/dT_max, which is the arterial pressure at dP/dT_max.

Skewness is the third moment of the blood pressure wave (i.e., the degree to which the wave is asymmetric with respect to its mid-point). Skewness is illustrated in FIG. 4. ("RAS" refers to the renin-angiotensin system.)

Heart rate (HR) is the number of detected beats per minute.

Augmentation Index (AIx) is the ratio between irregular pressure waveform amplitude to the total pulse pressure, and is a measure of wave reflection and arterial stiffness. AIx is illustrated in FIG. 3.

Diastolic Decay Time Constant (or Diastolic Decay Constant) (D_tau) is exponential pressure decay time (RC) during the diastolic period. D_tau is illustrated in FIG. 2.

Diastolic Average Slope (Dslope) is the average of the pressure derivative during the diastolic phase.

Systolic Pressure (SP) is the maximal pressure point of the entire pressure wave. SP is illustrated in FIG. 2 as Systolic Arterial Pressure (SAP).

Systolic Average Slope (Sslope) is the average of the pressure derivative during the systolic phase.

Pulse Pressure (PP) is the difference between SP and diastolic pressure (minimal pressure during the entire pressure wave). PP is illustrated in FIG. 2.

Systolic Duration Ratio (SDR) is the duration of systole as a proportion of the entire pressure wave. SDR is illustrated in FIG. 2.

More details regarding the parameters are included in the table of FIGS. 1A-C.

Reference is now made to FIGS. 5-9, which are flow charts showing at least some steps in respective techniques for use with nerve tissue, in accordance with some applications of the invention. Typically, these techniques are performed translluminally, e.g., by advancing a catheter into the renal artery and applying excitatory current, and optionally ablation energy, to renal nerve tissue via the wall of the renal artery. For example, these techniques may be performed using a system 120 (described with reference to FIG. 10), and/or in combination with apparatus and/or techniques described in one or more of the following references, which are incorporated herein by reference:

PCT application publication WO 2014/068577 to Gross et al., filed Nov. 3, 2013, and entitled "Controlled Tissue Ablation,"

PCT application publication WO 2015/170281 to Gross et al., filed May 7, 2015, and entitled "Controlled Tissue Ablation Techniques,"

U.S. patent application Ser. No. 14/794,737 to Gross et al., filed Jul. 8, 2015, and entitled "Electrical Signal-Based Electrode-Tissue Contact Detection," which published as US 2017/0007157, U.S. patent application Ser. No. 14/972,756 to Gross et al., filed Dec. 17, 2015, and entitled "Transluminal Electrode Catheters," which published as US 2017/0172651, U.S. patent application Ser. No. 15/001,615 to Gross et al., filed Jan. 20, 2016, and entitled "Catheter Guidance and Procedure Planning," which published as 2017/0202614.

Figure 5:
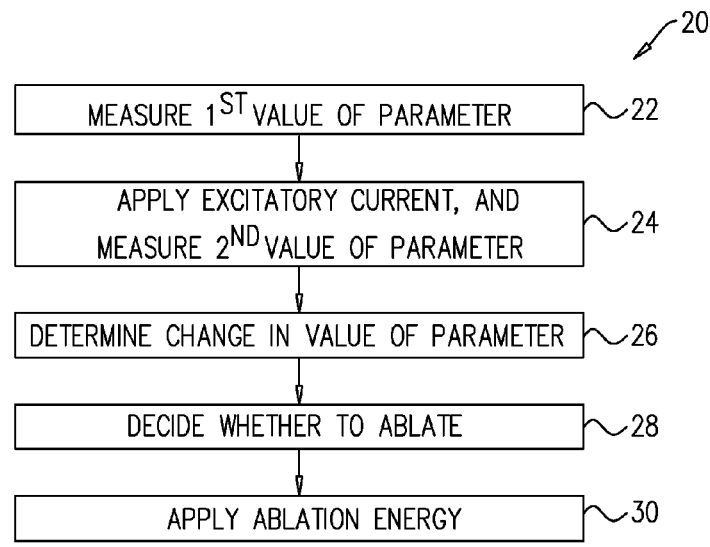
FIGS. 5, 6, 7, 8, and 9 are flow charts showing at least some steps in respective techniques for use with nerve tissue, in accordance with some applications of the invention.

As shown in FIG. 5, a method 20 is described, the method comprising: (i) applying an excitatory current to renal nerve fibers of a subject (box 24); (ii) determining a change in a parameter of the subject in response to the excitatory current (box 26), the parameter of the subject being a parameter that appears in the table of FIGS. 1A-C (and typically a parameter that appears in the top five in the table); (iii) in response to the change, deciding whether to ablate the renal nerve fibers (box 28); and (iv) in response to the deciding, applying ablation energy to the renal nerve fibers (box 30). Typically, the change in the parameter is determined by comparing a value of the parameter measured while the subject is at rest (e.g., before applying the excitatory current) (box 22) to a value measured during the application of the current (box 24).

For example, method 20, or a similar method, may be used to determine whether an individual subject is a suitable candidate for renal nerve ablation. Therefore, for some applications, a method comprises:

translumninally advancing a distal portion of a longitudinal member of a device into a renal artery of a subject;

operating the device to drive an electrode disposed on the distal portion of the longitudinal member to apply an excitatory current to nerve tissue of the renal artery;

receiving (i) a first value, the first value being indicative of a parameter of the subject (e.g., a parameter described herein) before a start of the application of the current, and (ii) a second value, the second value being indicative of the parameter of the subject after a start of the application of the current;

determining if a difference between the first value and the second value is smaller than a threshold difference; and in response to the determining:

only if the determined difference is smaller than the threshold difference, withdrawing the longitudinal member from the subject without having applied ablation energy to the renal artery.

For some applications, instead of withdrawing the longitudinal member from the subject, the longitudinal member is moved to another site within the subject and the process is repeated. For some applications, following several iterations of the process, if the determined difference at more than a threshold proportion of the sites (e.g., more than 50 percent, e.g., more than 60 percent, e.g., more than 70 percent, e.g., more than 80 percent, e.g., more than 90 percent) is smaller than the threshold difference, the longitudinal member is withdrawn from the subject without having applied ablation energy to the renal artery.

Figure 6:
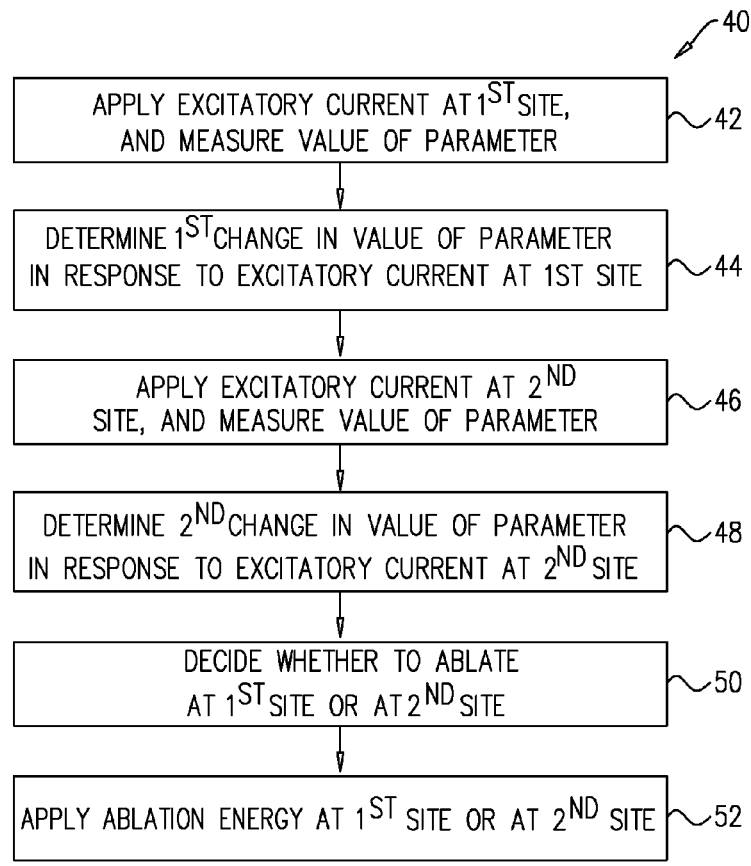

For some applications, method 20 is used at various locations within the renal artery, mutatis mutandis, e.g., to locate target renal nerve tissue (and optionally ablate it). Therefore, as shown in FIG. 6, a method 40 is described, the method being the same as method 20, wherein: (a) applying the excitatory current (box 24 of FIG. 5) comprises applying the excitatory current to renal nerve fibers proximate to a first location of a renal artery wall (box 42), (b) deciding whether to ablate the renal nerve fibers (box 28 of FIG. 5) comprises deciding whether to ablate the renal nerve fibers proximate to the first location (box 50), and (c) the method further comprises: (i) applying the excitatory current to renal nerve fibers proximate to a second location of a renal artery wall (box 46); (ii) determining a second change in the parameter in response to the excitatory current applied to the renal nerve fibers proximate to the second location (box 48); and (iii) in response to the second change, deciding whether to ablate the renal nerve fibers proximate to the second location (box 50). In response to deciding whether to ablate the renal nerve fibers proximate to the first location or the second location, ablation energy is applied to the renal nerve fibers (box 52). Box 44 of FIG. 6 corresponds to box 26 of FIG. 5 in the same way that boxes 42 and 50 of FIG. 6 correspond to boxes 24 and 28 of FIG. 5, respectively.

Figure 7:
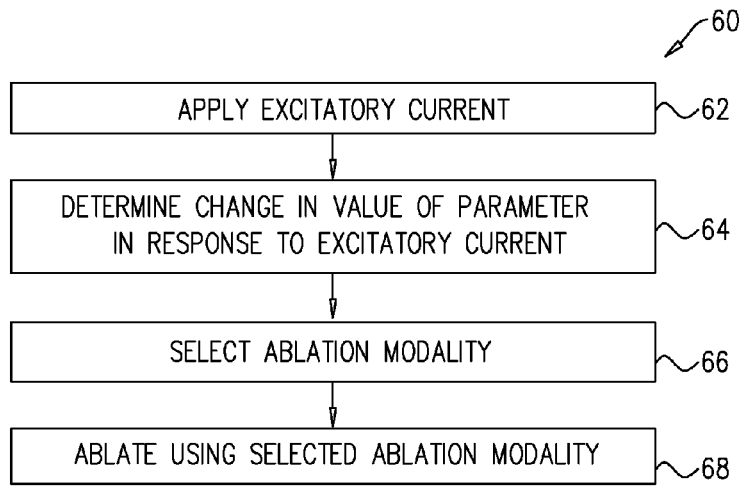

For some applications, a modality of ablation is selected in response to the change in value of the parameter. For example, the modality may be selected from radiofrequency (RF), ultrasound, heating, cooling, laser, chemical, or any other ablation modality known in the art. Therefore, as shown in FIG. 7, a method 60 is described, the method comprising (i) applying an excitatory current to renal nerve fibers of a subject (box 62); (ii) determining a change in a parameter of the subject in response to the excitatory current (box 64), the parameter of the subject being a parameter that appears in the table of FIGS. 1A-C (and typically a parameter that appears in the top five in the table); (iii) in response to the change, selecting an ablation modality from a plurality of ablation modalities (66); and (iv) in response to the selecting, ablating the renal nerve fibers using the selected ablation modality (box 68).

Figure 8:
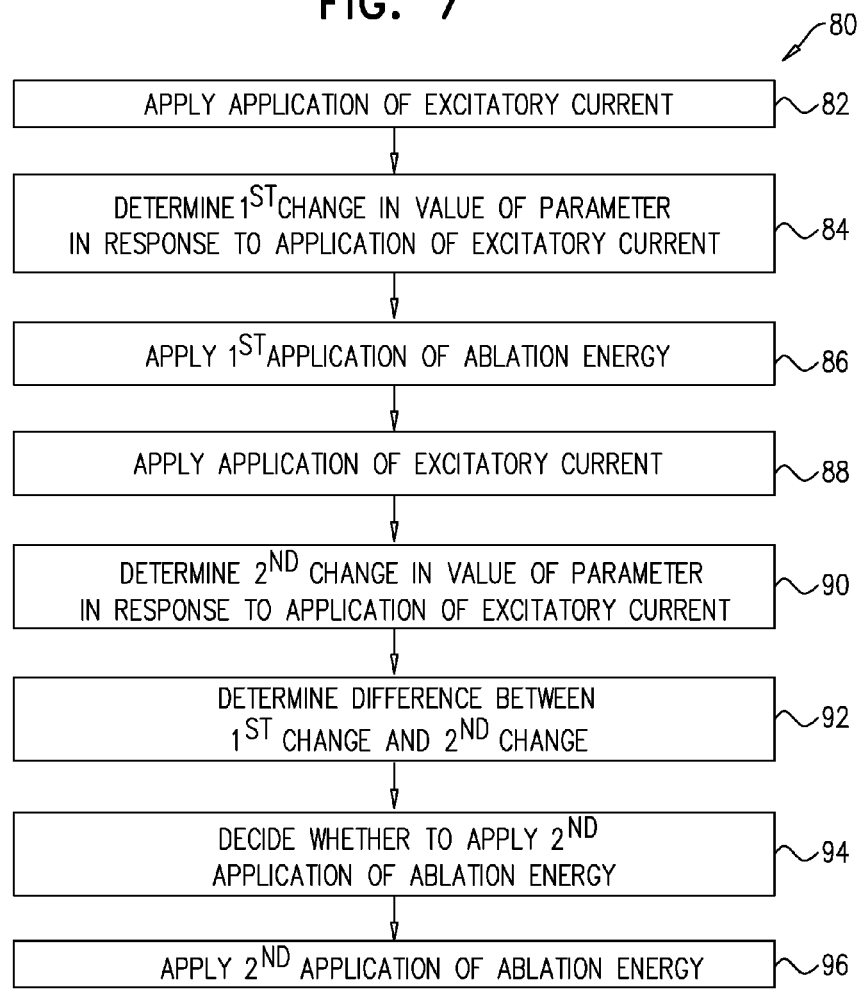

For some applications, the parameters in the table of FIGS. 1A-C are used to monitor the progress of an ablation process. For example, ablation energy may be applied to the nerve tissue iteratively, and measurement of the parameter after each application may be used to determine whether the nerve tissue has become sufficiently ablated (e.g., sufficiently unable to propagate action potentials therealong). Therefore, as shown in FIG. 8, a method is described, the method comprising: (i) applying an application of excitatory current to renal nerve fibers of a subject (box 82); (ii) determining a first change in a parameter of the subject in response to the application of excitatory current (box 84), the parameter of the subject being a parameter that appears in the table of FIGS. 1A-C (and typically a parameter that appears in the top five in the table); (iii) subsequently, applying a first application of ablating energy to the renal nerve fibers (box 86); (iv) subsequently, applying another application of excitatory current to renal nerve fibers of a subject (box 88); (v) determining a second change in the parameter in response to the second application of excitatory current (box 90); (vi) determining a difference between the first change and the second change (box 92); (vii) deciding whether to apply a second application of ablation energy to the renal nerve fibers (box 94); and (viii) in response to the deciding, applying the second application of ablation energy to the renal nerve fibers (box 96).

Figure 9:
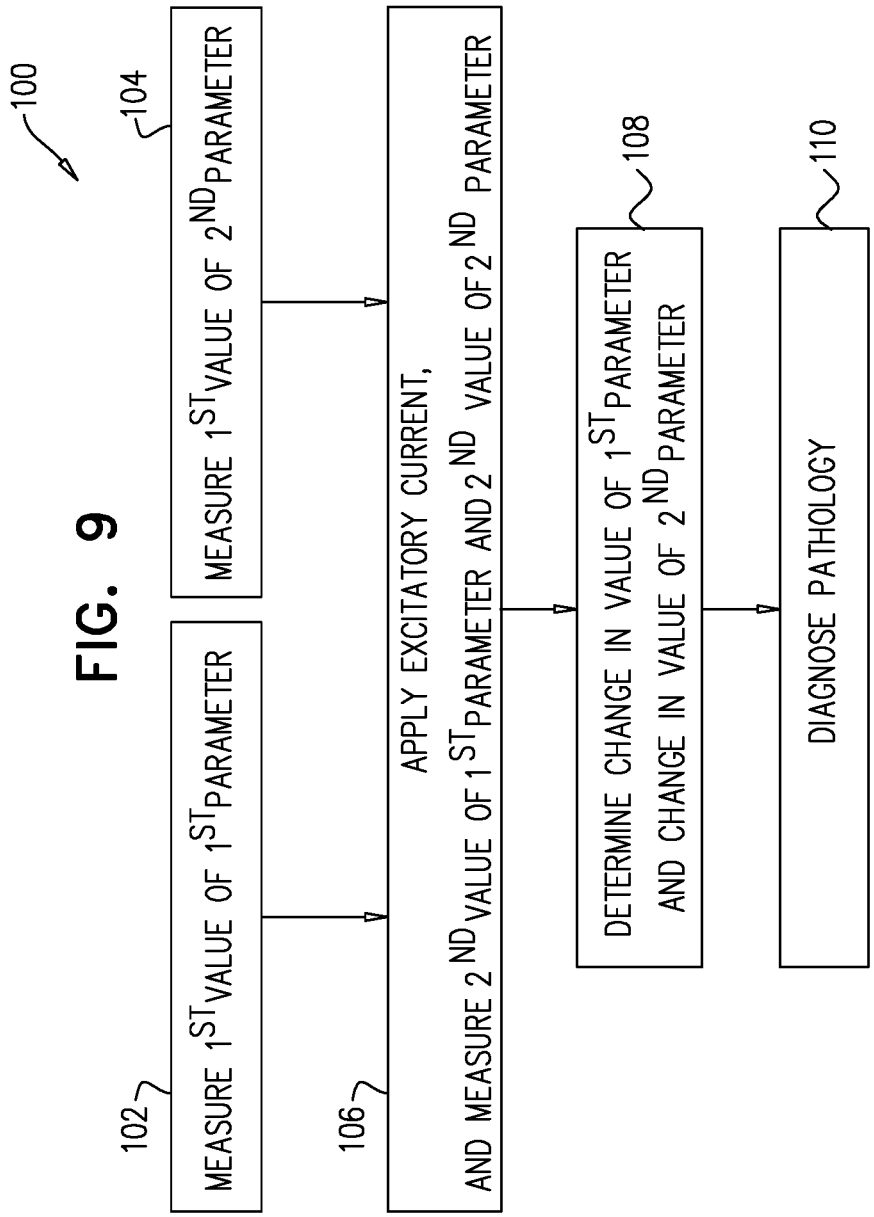

Because, as described hereinabove and in the table of FIGS. 1A-C, the parameters relate to different physiological aspects (e.g., properties), it is hypothesized that determining how the parameters respond to excitation of renal nerve tissue may facilitate more detailed understanding and/or definition of the particular condition of the subject (e.g., enabling a more specific diagnosis of the condition). It is further hypothesized that taking into account two or more of the parameters will be further facilitative. As shown in FIG. 9, a method 100 is described, the method comprising: (i) transluminally advancing an electrode into a renal artery of a subject; (ii) while the subject is at rest, measuring a first value of a first parameter (box 102) and a first value of a second parameter (box 104), the first parameter and the second parameter selected from the parameters that appear in the table of FIGS. 1A-C (and typically those that appear in the top five in the table); (iii) applying an excitatory current to renal nerve fibers of a subject, and while applying the excitatory current, measuring a second value of the first parameter and a second value of the second parameter (box 106); (iv) determining (a) a first difference between the first value of the first parameter and the second value of the first parameter, and (b) a second difference between the first value of the second parameter and the second value of the second parameter (box 108); and (v) in response to the first difference and the second difference, diagnosing a pathology of the subject (110).

For some applications, differences between first and second values of only two parameters from the table are used for diagnosing the pathology (e.g., the first and second parameters in the above paragraph). For some applications more than two parameters (e.g., at least three parameters, e.g., at least four parameters, such as at least five parameters) from the table (and typically from the top five in the table) are used.

Reference is again made to FIGS. 1A-8. Although methods 20, 40, 60, and 80 are generally described with reference to "a parameter," it is to be understood that the scope of the invention includes the use of more than one of the parameters in the table of FIGS. 1A-C (typically in the top five parameters of the table). Furthermore, methods 20, 40, 60, 80, and 100 may be further facilitated by taking into account other parameters of the subject, including other blood pressure parameters, and non-blood pressure parameters.

Reference is again made to FIGS. 1A-9. Described hereinabove are parameter values measured before application of the excitatory current, and parameter values measured during application of the excitatory current. It is to be noted that for some applications of the invention, the timing of these two measurements may differ from a strict definition of these timings, in that, for example, a "before" value of the parameter may be measured soon after the beginning of application of the excitatory current, before the action potentials initiated by the excitatory current have begun to affect the parameter. Similarly, a "during" value of the parameter may be measured soon after the end of application of the excitatory current, before the parameter has begun to return toward the "before" value.

Reference is again made to FIGS. 1A-9. The excitatory current described hereinabove is to be understood as a current that initiates action potentials in the nerve tissue. Typically, the excitatory current has a frequency of greater than 1 Hz and/or less than 100 Hz, such as between 1 and 100 Hz, e.g., between 10 and 100 Hz. For some applications, the ablation energy described hereinabove is RF energy, e.g., an RF current having a frequency of above 5 kHz and/or below 1 GHz, such as between 5 kHz and 1 GHz (e.g., 10 kHz-10 MHz, e.g., 50 kHz-1 MHz, e.g., 300 kHz-1 MHz, e.g., 300 kHz-500 kHz).

Reference is again made to FIGS. 5-9. For some applications, the techniques described hereinabove are performed generally manually by a physician (alone, or with assistance). For example, a commercially-available arterial blood pressure sensor may be used to monitor arterial blood pressure; the output may be separately analyzed (e.g., manually, or using a computer) to measure the values of the parameter(s); and the change in the value of the parameter(s) may be separately determined (e.g., manually, or using a computer).

Figure 10:
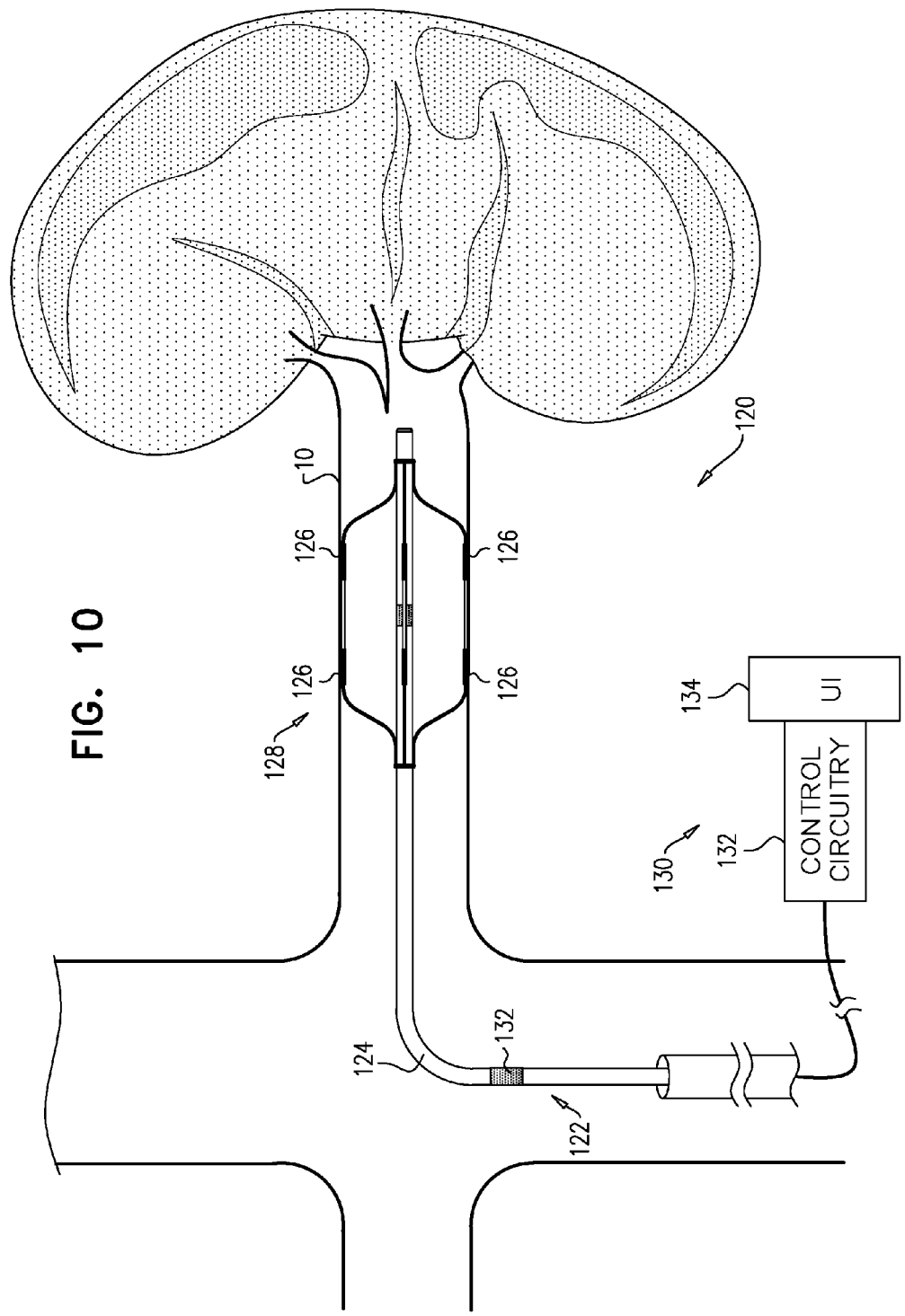
FIG. 10 is a schematic illustration of a system for ablating and/or stimulating nerve tissue of a blood vessel of a subject, in accordance with some applications of the present invention.

Reference is now made to FIG. 10, which is a schematic illustration of a system 120 for ablating and/or stimulating nerve tissue of a blood vessel of a subject, such as a renal artery 10, in accordance with some applications of the present invention. For some applications, the techniques described hereinabove are performed generally automatically by a device such as system 120, comprising a transluminal electrode catheter 122 that comprises a transluminally-advanceable longitudinal member (e.g., a flexible shaft) 124, one or more electrodes 126 at a distal portion 128 of the longitudinal member, and a (typically extracorporeal) control unit 130 that comprises control circuitry 132, and is electrically coupled to the catheter. Control unit 130 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. Such program code and/or data, when provided to the control unit, produce a machine or special-purpose computer, configured to perform the tasks described herein. Typically, control unit 130 is connected to an arterial blood pressure sensor 132 (which may be disposed on longitudinal member 124), and is configured to receive signals from the sensor.

Typically, control unit 30 comprises a user interface 134, which is configured to receive user input (e.g., activation of the system) and/or to output measurements and/or status.

The control unit automatically performs one or more of the following steps: (1) deriving the value of the parameter (e.g., from raw pressure data from the pressure sensor), (2) driving the electrodes to apply the excitatory current, (3) determining a change in the parameter value in response to the excitatory current, and (4) providing an output via an interface. For some applications, the output indicates the change in the parameter value in response to the excitatory current (e.g., as an absolute value, as a relative value, or as an indication of whether the change exceeds a threshold change), and based on the output the physician decides whether to ablate.

For some applications, the control unit drives the electrodes to apply the ablation energy, either automatically in response to the determined change in the parameter value, or when activated by the physician. That is, for some applications, the same device is configured and used to apply the excitatory current and to apply the ablation energy (and typically to measure the arterial blood pressure). For some applications, the device is not configured or used to apply both the excitatory current and the ablation energy. For example, a separate ablation device may be used, either during the same general procedure (e.g., without the subject leaving the treatment room), or at another time.

Therefore, for some applications, apparatus comprises:
a transluminal electrode catheter 122, comprising:
  a flexible shaft 124, dimensioned for advancement of a distal portion 128 of the shaft into a renal artery 10 of a subject;
  a plurality of electrodes 126 disposed at the distal portion of the shaft; and
  an arterial blood pressure sensor 132; and
a control unit 130, electrically coupled to the catheter.
For some applications, control unit 130 is configured to:
  use sensor 124 to measure a first value of a parameter of the subject while the subject is at rest (the parameter being a parameter described herein), drive at least one of the electrodes 126 to apply an excitatory current to renal nerve fibers of the subject, while applying the excitatory current, use the blood pressure sensor to measure a second value of the parameter, determine if a difference between the first value and the second value is greater than a threshold difference, and in response to the determining:
only if the determined difference is greater than the threshold difference, enable an ablation function of the control unit.

The ablation function of control unit 130 can be activated only while enabled. Upon its activation, the ablation function of the control unit drives at least one of the electrodes to apply ablation energy to the renal nerve fibers (through the wall of renal artery 10). For some applications, control unit 130 activates the ablation function automatically upon the enabling of the ablation function. For some applications, control unit enables the ablation function, but activation of the ablation function requires subsequent user input (e.g., via interface 134).

For some applications, the devices described hereinabove are similar to those described in PCT application publication WO 2014/068577 to Gross et al., filed Nov. 3, 2013, and entitled "Controlled Tissue Ablation," and/or a PCT application to Yossi GROSS et al., filed on even date herewith, and entitled "Controlled Tissue Ablation Techniques," both of which are incorporated herein by reference.

It will be understood that, although the terms "first," "second," etc. may be used in the present application (including the specification and the claims) to describe various elements and/or directions, these terms should not be limiting. These terms are only used to distinguish one element and/or direction from another. Thus, a "first" element described herein could also be termed a "second" element without departing from the teachings of the present disclosure.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
applying an excitatory current to renal nerve fibers of a subject;
determining a change in a parameter of the subject in response to the excitatory current, the parameter being a fastest rate of increase in arterial pressure during a systolic upstroke of an arterial pressure wave of the subject;
in response to the change, deciding whether to ablate or to not ablate the renal nerve fibers; and
in response to a decision to ablate, applying ablation energy to the renal nerve fibers.

2. The method according to claim 1, wherein:
the renal nerve fibers comprise renal nerve fibers proximate to a first location of a renal artery wall and renal nerve fibers proximate to a second location of the renal artery wall;
applying the excitatory current comprises applying the excitatory current to the renal nerve fibers proximate to the first location of the renal artery wall, deciding whether to ablate or to not ablate the renal nerve fibers comprises deciding whether to ablate or to not ablate the renal nerve fibers proximate to the first location of the renal artery wall, and the method further comprises:
applying the excitatory current to the renal nerve fibers proximate to the second location of the renal artery wall;
determining a second change in the parameter in response to the excitatory current applied to the renal nerve fibers proximate to the second location of the renal artery wall; and
in response to the second change, making a second decision to ablate or to not ablate the renal nerve fibers proximate to the second location of the renal artery wall.

3. A method, comprising:
measuring a first value of a parameter of a subject while the subject is at rest, the parameter being a fastest rate of increase in arterial pressure during a systolic upstroke of an arterial pressure wave of the subject;
applying an excitatory current to renal nerve fibers of the subject;
while applying the excitatory current, measuring a second value of the parameter;
in response to a difference between the first value and the second value, deciding whether to ablate or to not ablate the renal nerve fibers; and
in response to a decision to ablate, applying ablation energy to the renal nerve fibers.

4. A method, comprising:
applying an excitatory current to renal nerve fibers of a subject;
determining a change in a parameter of the subject in response to the excitatory current, the parameter being a fastest rate of increase in arterial pressure during a systolic upstroke of an arterial pressure wave of the subject;
in response to the change, selecting an ablation modality from a plurality of ablation modalities; and
in response to the selecting, ablating the renal nerve fibers using the selected ablation modality.

5. A method, comprising:
applying a first application of excitatory current to renal nerve fibers of a subject;
determining a first change in a parameter of the subject in response to the first application of excitatory current, the parameter being a fastest rate of increase in arterial pressure during a systolic upstroke of an arterial pressure wave of the subject;
subsequently, applying a first application of ablation energy to the renal nerve fibers;
subsequently, applying a second application of excitatory current to the renal nerve fibers of the subject;
determining a second change in the parameter in response to the second application of excitatory current;
determining a difference between the first change and the second change;
deciding whether to apply or to not apply a second application of ablation energy to the renal nerve fibers; and
in response to a decision to apply the second application of ablation energy, applying the second application of ablation energy to the renal nerve fibers.

6. A method, comprising:
transluminally advancing a distal portion of a longitudinal member of a device into a renal artery of a subject;

operating the device to drive an electrode disposed on the distal portion of the longitudinal member to apply an excitatory current to nerve tissue of the renal artery;

receiving (i) a first value, the first value being indicative of a parameter of the subject before a start of the application of the excitatory current, and (ii) a second value, the second value being indicative of the parameter of the subject after the start of the application of the excitatory current, the parameter being a fastest rate of increase in arterial pressure during a systolic upstroke of an arterial pressure wave of the subject;

determining if a difference between the first value and the second value is smaller than a threshold difference; and in response to the determining:

only if the determined difference is smaller than the threshold difference, withdrawing the longitudinal member from the subject without having applied ablation energy to the renal artery.

7. Apparatus comprising:

a transluminal electrode catheter, comprising:

a flexible shaft, dimensioned for advancement of a distal portion of the shaft into a renal artery of a subject;

a plurality of electrodes disposed at the distal portion of the shaft;

an arterial blood pressure sensor; and a control unit, electrically coupled to the catheter, and configured to:

use the arterial blood pressure sensor to measure a first value of a parameter of the subject while the subject is at rest, the parameter being a fastest rate of increase in arterial pressure during a systolic upstroke of an arterial pressure wave of the subject, drive at least one of the electrodes to apply an excitatory current to renal nerve fibers of the subject, while applying the excitatory current, use the arterial blood pressure sensor to measure a second value of the parameter, determine if a difference between the first value and the second value is greater than a threshold difference, and in response to the determining:

only if the determined difference is greater than the threshold difference, enable an ablation function of the control unit and drive at least one of the electrodes to apply ablation energy to the renal nerve fibers.

* * * * *